United States Patent
Takishita et al.

(10) Patent No.: US 11,543,747 B2
(45) Date of Patent: Jan. 3, 2023

(54) COMPOSITION, COLOR FILTER, AND HEMOGLOBIN SENSOR

(71) Applicant: FUJIFILM Corporation, Tokyo (JP)

(72) Inventors: Hirotaka Takishita, Shizuoka (JP); Kazuya Oota, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 546 days.

(21) Appl. No.: 16/568,871

(22) Filed: Sep. 12, 2019

(65) Prior Publication Data

US 2020/0004140 A1 Jan. 2, 2020

Related U.S. Application Data

(63) Continuation of application No. PCT/JP2018/008174, filed on Mar. 2, 2018.

(30) Foreign Application Priority Data

Mar. 24, 2017 (JP) .............................. JP2017-060057

(51) Int. Cl.
| | |
|---|---|
| *G03F 7/00* | (2006.01) |
| *G02B 5/22* | (2006.01) |
| *G01N 33/49* | (2006.01) |
| *G03F 7/033* | (2006.01) |

(52) U.S. Cl.
CPC ............ *G03F 7/0007* (2013.01); *G01N 33/49* (2013.01); *G02B 5/22* (2013.01); *G03F 7/033* (2013.01)

(58) Field of Classification Search
CPC ....... G03F 7/0007; G03F 7/033; G01N 33/49; G02B 5/22
USPC ...................................................... 252/586
See application file for complete search history.

(56) References Cited

U.S. PATENT DOCUMENTS

| | | | | |
|---|---|---|---|---|
| 2008/0079807 | A1* | 4/2008 | Inuiya | H01L 27/14621 348/70 |
| 2016/0216604 | A1 | 7/2016 | Fujita et al. | |

FOREIGN PATENT DOCUMENTS

| | | | | |
|---|---|---|---|---|
| CN | 105593246 | A | 5/2016 | |
| CN | 106537906 | A | 3/2017 | |
| JP | 2006-045399 | A | 2/2006 | |
| JP | 2006-104243 | A | 4/2006 | |
| JP | 2006104243 | A * | 4/2006 | |
| JP | 2008-085807 | A | 4/2008 | |
| JP | 2010-026107 | A | 2/2010 | |
| JP | 2010-237427 | A | 10/2010 | |
| JP | 2011-053119 | A | 3/2011 | |
| JP | 2011-242425 | A | 12/2011 | |
| JP | 2013-092684 | A | 5/2013 | |
| JP | 2013092684 | A * | 5/2013 | |
| JP | 2013-195986 | A | 9/2013 | |
| JP | 2013-225132 | A | 10/2013 | |
| JP | 2013225132 | A * | 10/2013 | ............. C09D 5/035 |
| JP | 2016-040363 | A | 3/2016 | |
| KR | 10-2016-0048910 | A | 5/2016 | |
| TW | 201522521 | A | 6/2015 | |
| WO | 2015/046285 | A1 | 4/2015 | |
| WO | 2016/009925 | A1 | 1/2016 | |
| WO | 2016/013520 | A1 | 1/2016 | |
| WO | WO-2016009925 | A1 * | 1/2016 | ............. G03B 11/00 |

OTHER PUBLICATIONS

Communication dated Jan. 28, 2020, from the Japanese Patent Office in Application No. 2019-507499.
International Search Report dated May 22, 2018 from the International Searching Authority in counterpart International Application No. PCT/JP2018/008174.
International Preliminary Report on Patentability dated Sep. 24, 2019 from the International Bureau in counterpart International Application No. PCT/JP2018/008174.
Written Opinion dated May 22, 2018 from the International Bureau in counterpart International Application No. PCT/JP2018/008174.
Office Action dated Jun. 16, 2020 in Japanese Application No. 2019-507499.

\* cited by examiner

*Primary Examiner* — Ling Siu Choi
*Assistant Examiner* — Ronald Grinsted
(74) *Attorney, Agent, or Firm* — Sughrue Mion, PLLC

(57) ABSTRACT

Provided are a composition, in which, in a case where an absorbance of 500 nm is $A_{500}$, an absorbance of 580 nm is $B_{580}$, and an absorbance of 600 nm is $C_{600}$, an absorbance of $A_{500}/B_{580}$ is 2.0 or more, and $C_{600}/B_{580}$ is 1.5 or more, a color filter, and a hemoglobin sensor having the color filter.

17 Claims, No Drawings

COMPOSITION, COLOR FILTER, AND HEMOGLOBIN SENSOR

CROSS-REFERENCE TO RELATED APPLICATIONS

This application is a continuation application of International Application No. PCT/JP2018/008174, filed Mar. 2, 2018, the disclosure of which is incorporated herein by reference in its entirety. Further, this application claims priority from Japanese Patent Application No. 2017-060057, filed Mar. 24, 2017, the disclosure of which is incorporated herein by reference in its entirety.

BACKGROUND OF THE INVENTION

1. Field of the Invention

The present disclosure relates to a composition, a color filter, and a hemoglobin sensor.

2. Description of the Related Art

At present, a color filter is used in various applications such as a monitor application in a liquid crystal display device and an organic electroluminescence (EL) element, and an application in an image sensor (solid-state imaging device). A color filter is generally manufactured by mixing a polymerizable compound, a polymerization initiator, a resin, and other components with a pigment dispersion composition obtained by dispersing an organic pigment or an inorganic pigment to obtain a composition, and forming a coloration pattern by photolithography or the like, by using the composition.

For example, there are known compositions disclosed in the following documents, as a composition used in manufacturing of a color filter.

JP2011-242425A discloses a green colorant composition for a color filter that contains at least a resin, a solvent, and a pigment; containing C. I. Pigment Blue 16 and a yellow pigment as a pigment, in which a content of C. I. Pigment Blue 16 in the total pigment in the composition is 5 to 40 mass %.

JP2010-237427A discloses a photocuring coloring composition including C. I. Pigment Green 7, phthalocyanine blue of at least one selected from C. I. Pigment Blue 15:3, C. I. Pigment Blue 15:4, and aluminum phthalocyanine blue, at least one isoindoline-based pigment selected from C. I. Pigment Yellow 185 and C. I. Pigment Yellow 139, and a photopolymerizable compound.

JP2010-026107A discloses a cyan pigment dispersion liquid for a color filter containing a pigment including a yellow pigment and at least including C. I. Pigment Green 58 and a blue pigment, a pigment dispersing agent, and a solvent.

JP2006-104243A discloses a green coloring composition having spectral characteristics in which, in a case where a coating film is formed such that a spectral transmittance at 650 nm is 5%, a wavelength of a spectral transmittance at 50% on a short wavelength side in the coating film is in the range of 530 nm to 550 nm, a wavelength of 50% of the spectral transmittance on a long wavelength side is in a range of 580 nm to 600 nm, and a maximum value of a spectral transmittance is 70% or more.

JP2013-195986A discloses a coloring composition for a solid-state imaging device include a green pigment and a yellow pigment, in which the green pigment includes C. I. Pigment Green 36, and the yellow pigment includes two or more selected from the group consisting of C. I. Pigment Yellow 83, C. I. Pigment Yellow 110, C. I. Pigment Yellow 138, C. I. Pigment Yellow 139, and C. I. Pigment Yellow 150.

JP2011-053119A discloses a method of observing a tissue of a small laboratory animal, comprising: a step of irradiating a part to be observed of the tissue with illumination light including a visible range; and a step of obtaining an image of the part to be observed by return light of the illumination light from the part to be observed that can be obtained by using an optical microscope, in image pick-up means, in which the return light incident on the image pick-up means is limited such that a wavelength range of is narrowed down to a predetermined wavelength range of green light in order to obtain the part to be observed of the tissue.

SUMMARY OF THE INVENTION

One application of the image sensor is a hemoglobin sensor that recognizes hemoglobin in blood.

By recognizing hemoglobin by the hemoglobin sensor, for example, it is considered that blood vessel authentication (for example, vein authentication), measurement of a blood oxygen concentration, measurement of a pulse, measurement of a hemoglobin amount, human skin authentication, and the like becomes possible.

Here, it is known that, with respect to the hemoglobin, the absorption wavelength in the range of visible light (400 nm to 700 nm) changes due to the difference in a valence or a binding ligand of included iron, such as oxygenated hemoglobin (methemoglobin), oxygenated hemoglobin (oxyhemoglobin), deoxygenated (reduced) hemoglobin (deoxyhemoglobin), and cyanmethemoglobin.

For example, it is known that oxygenated hemoglobin has maximum absorption wavelengths at around 540 nm and around 580 nm, and has weak absorption (the absorbance is small) of light at a wavelength of around 500 nm.

Therefore, for example, it is considered that hemoglobin can be recognized with visible light by using a composition that specifically transmits light of a wavelength of around 500 nm, a composition that specifically transmits light of a wavelength of around 580 nm, or the like.

Similarly, for example, it is considered that, by using a color filter that specifically transmits light of a wavelength of around 500 nm, a color filter that specifically transmits light of a wavelength of around 580 nm, and the like, hemoglobin recognition by visible light becomes possible.

It is considered that all of the compositions disclosed in the above patent documents have low specificity to the above wavelength and are difficult to use for recognizing hemoglobin with visible light.

JP2011-053119A discloses a method of recognizing hemoglobin by limiting the wavelength range of the return light incident on the image pick-up means by using a band pass filter to light in a wavelength range of 510 nm to 550 nm by usng a band pass filter.

As the band pass filter in the related art that is used in the above method, a vapor deposition film is used. However, according to the composition according to the present disclosure, for example, hemoglobin can be recognized by a very simple method such as coating with the composition.

For example, in the case of oxygenated hemoglobin, the light absorption coefficient at around 580 nm is larger than that at around 540 nm, and in a case of being photographed using only light having a wavelength of around 540 nm as disclosed in JP2011-053119A, recognition of hemoglobin is insufficient in some cases.

The problem to be solved by an embodiment of the present invention is to provide a composition that enables recognition of hemoglobin by visible light.

The problem to be solved by another embodiment of the present invention is to provide a color filter that enables recognition of hemoglobin by visible light, and a hemoglobin sensor having the color filter.

Means for solving the above problems include the following aspects.

<1> A composition, wherein, in a case where an absorbance at 500 nm is $A_{500}$, an absorbance at 580 nm is $B_{580}$, and an absorbance at 600 nm is $C_{600}$, $A_{500}/B_{580}$ is 2.0 or more, and $C_{600}/B_{580}$ is 1.5 or more.

<2> The composition according to <1>, in which a minimum absorption wavelength in a wavelength range of 400 nm to 700 nm is present in a range of 575 nm to 585 nm.

<3> The composition according to <1> or <2>, comprising: a green colorant; and an orange colorant, in which a total content of the green colorant and the orange colorant is 80 mass % or more with respect to a total mass of colorants included in the composition.

<4> A composition, in which an absorbance at 500 nm is $A_{500}$, an absorbance at 580 nm is $B_{580}$, and an absorbance at 600 nm is $C_{600}$, $B_{580}/A_{500}$ is 5.0 or more, and $C_{600}/A_{500}$ is 5.0 or more.

<5> The composition according to <4>, in which a minimum absorption wavelength in a wavelength range of 400 nm to 700 nm is present in a range of 490 nm to 510 nm.

<6> The composition according to <4> or <5>, comprising: a blue colorant; and a yellow colorant, in which a total content of the blue colorant and the yellow colorant is 80 mass % or more with respect to a total mass of colorants included in the composition, and a mass ratio of the blue colorant and the yellow colorant (the blue colorant : the yellow colorant) is from 70:30 to 30:70.

<7> The composition according to any one of <1> to <6>, comprising: an alkali soluble resin.

<8> The composition according to any one of <1> to <7>, comprising: a polymerizable compound; and a photopolymerization initiator.

<9> The composition according to any one of <1> to <8>, which is for manufacturing a color filter.

<10> A color filter, using the composition according to any one of <1> to <9>. <11> A color filter, comprising: at least two pixels selected from the group consisting of, in a case where an absorbance at 500 nm is $A_{500}$, an absorbance at 580 nm is $B_{580}$, an absorbance at 600 nm is $C_{600}$, and an absorbance at 540 nm is $D_{540}$:

a color filter 1 having $A_{500}/B_{580}$ of 2.0 or more, and $C_{600}/B_{580}$ of 1.5 or more, a color filter 2 having $B_{580}/A_{500}$ of 5.0 or more, and $C_{600}/A_{500}$ of 5.0 or more, a color filter 3 having $A_{500}/D_{540}$ of 1.5 or more, and $C_{600}/D_{540}$ of 3.0 or more, and a color filter 4 having $A_{500}/C_{600}$ of 5.0 or more, and $B_{580}/C_{600}$ of 3.0 or more, and wherein the color filter at least comprises the color filter 1 or the color filter 2.

<12> A hemoglobin sensor comprising: the color filter according to <10> or <11>.

According to an embodiment of the present invention, it is possible to provide a composition that can cause hemoglobin to be recognized by visible light.

According to another embodiment of the present invention, it is possible to provide a color filter that can cause hemoglobin to be recognized by visible light and a hemoglobin sensor having the color filter.

DESCRIPTION OF THE PREFERRED EMBODIMENTS

Hereinafter, the content of the present disclosure is described.

In the present specification, a numerical range represented using "to" means a range including numerical values described before and after "to" as the lower limit value and the upper limit value.

In the present specification, "(meth) acryl" represents both or either of acrylic and methacryl, and "(meth) acrylate" represents both or either of acrylate and methacrylate.

In the present specification, with respect to an amount of each component in a composition, in a case where a plurality of materials corresponding to the component are present, unless described otherwise, the amount means a total amount of the plurality of corresponding materials that are present in the composition.

In the present specification, the expression "step" includes not only an independent step but also include a case where the step is not clearly distinguished from other steps as long as the intended purpose of the step is achieved.

In the notation of groups (atomic groups) in the present specification, notations not describing substitution and non-substitution include those not having a substituent as well as those having a substituent. For example, the "alkyl group" includes not only an alkyl group not having a substituent (unsubstituted alkyl group) but also an alkyl group having a substituent (substituted alkyl group).

A chemical structural formula in the present specification is described by a simplified structural formula in which a hydrogen atom is omitted, in some cases.

In the present disclosure, "mass %" and "weight%" have the same meaning, and "a part by mass" and "a part by weight" have the same meaning.

In the present disclosure, a combination of two or more preferable aspect is a more preferable aspect.

(Composition)

In a first aspect of the composition according to the present embodiment, in a case where the absorbance at 500 nm is $A_{500}$, the absorbance at 580 nm is $B_{580}$, and the absorbance at 600 nm is $C_{600}$, $A_{500}/B_{580}$ is 2.0 or more, and $C_{600}/B_{580}$ is 1.5 or more.

In a second aspect of the composition according to the present embodiment, in a case where the absorbance at 500 nm is $A_{500}$, the absorbance at 580 nm is $B_{580}$, and the absorbance at 600 nm is $C_{600}$, $B_{580}/A_{500}$ is 5.0 or more, and $C_{600}/A_{500}$ is 5.0 or more.

Hereinafter, the composition according to the first aspect is also referred to as a "first composition", and the composition according to the second aspect is also referred to as a "second composition".

In the related art, the hemoglobin is recognized by using properties of absorbing the infrared light of hemoglobin and using a silicon photodiode having photosensitivity in an infrared region (for example, 800 nm to 1,000 nm).

However, since silicon photodiodes have low sensitivity to infrared light, for example, in a case where an inexpensive and general white light source is used as a light source, a light amount of infrared light included in the white light source is lower than that of visible light, and thus there is a problem in that hemoglobin is poorly recognized.

Therefore, as a result of diligent research, the present inventors have found that hemoglobin can be recognized by light with the composition according to the present embodiment.

In the first composition, $A_{500}/B_{580}$ is 2.0 or more, $C_{600}/B_{580}$ is 1.5 or more, and for example, the first composition can transmit light of 580 nm which is a maximum absorption wavelength of oxygenated hemoglobin. In the second composition, $B_{580}/A_{500}$ is 5.0 or more, and $C_{600}/A_{500}$ is 5.0 or more, and for example, the second composition can transmit light of 500 nm which has small absorption of oxygenated hemoglobin. Thus, it is considered that hemoglobin can be recognized by visible light by using either or both of these compositions.

As described in JP2011-053119A, a band pass filter by vapor deposition is used for recognizing hemoglobin in the related art.

It is useful that the first composition or the second composition according to the embodiment of the present disclosure is a composition capable of forming a coloration pattern by photolithography, unlike the filter by the vapor deposition, because a color filter that can be disposed in a solid-state imaging device can be formed. In the color filter, there is also an advantage in that band pass filters or the like transmitting a plurality of different wavelengths can be easily arrayed in combination.

For example, either or both of the first composition or the second composition according to the embodiment the present disclosure is made to a color filter having pixels transmitting a plurality of different wavelengths which is provided as a color filter according to the embodiment of the present disclosure described below, and thus the recognition of hemoglobin can be improved, and the state of hemoglobin can be identified.

(First Composition)

In the first composition according to the present embodiment, in a case where the absorbance at 500 nm is $A_{500}$, the absorbance at 580 nm is $B_{580}$, and the absorbance at 600 nm is $C_{600}$, $A_{500}/B_{580}$ is 2.0 or more, and $C_{600}/B_{580}$ is 1.5 or more.

The first composition is preferably a photosensitive composition, and is more preferably a negative photosensitive composition in view of forming a color filter.

In the present embodiment, the expression "photosensitive" refers to properties that the solubility in a liquid (for example, a developer) is changed by the irradiation of light.

The first composition is preferably for manufacturing a color filter.

<Absorbance and Minimum Absorption Wavelength>

In the present embodiment, the absorbance of the composition and the minimum absorption wavelength are values measured by the following method.

A glass substrate is coated with the composition at a rotational speed at which the film thickness after drying becomes 1.0 μm by using a spin coater, and a heat treatment (prebaking) is performed for 120 seconds by using a hot plate at 100° C. so as to obtain a dried film. Absorbance of the dried film obtained as described above in the visible light region at a wavelength of 400 nm to 700 nm in the thickness direction is obtained by using a spectrophotometer of an ultraviolet visible near infrared spectrophotometer U-4150 (manufactured by Hitachi High-Technologies Corporation) at 1 nm intervals. The absorbance is a value obtained by subtracting the absorbance of only the glass substrate which is not coated with the composition as a reference value (reference).

In view of recognition of hemoglobin, $A_{500}/B_{580}$ is 2.0 or more, preferably 2.0 to 10,000, and more preferably 3.0 to 10,000.

In view of recognition of hemoglobin, $C_{600}/B_{580}$ is 1.5 or more, preferably 1.5 to 10,000, and more preferably 1.6 to 10,000.

In view of recognition of hemoglobin, $B_{580}$ is preferably 0.003 to 0.5, more preferably 0.003 to 0.4, and even more preferably 0.003 to 0.3.

$A_{500}/B_{580}$, $C_{600}/B_{580}$, and $B_{580}$ are adjusted according to kinds and contents of the colorant contained in the composition.

In view of recognition of hemoglobin, in the first composition, the minimum absorption wavelength in the wavelength range of 400 nm to 700 nm is preferably present in the range of 565 nm to 595 nm, more preferably present in the range of 570 nm to 590 nm, and even more preferably present in the range of 575 nm to 585 nm.

The absorbance at the minimum absorption wavelength is preferably 0.4 or less, more preferably 0.3 or less, and even more preferably 0.25 or less.

The lower limit of the absorbance is not particularly limited, and may be 0 or more.

<Colorant>

The first composition according to the present embodiment preferably contains a green colorant and an orange colorant. In a case of containing a green colorant and an orange colorant, a composition in which $A_{500}/B_{580}$ is 2.0 or more, and $C_{600}/B_{580}$ is 1.5 or more can be easily obtained.

Details of each colorant are described below.

[Green Colorant]

As the green colorant, a well-known colorant can be used without particular limitation, but an organic pigment is preferable.

Examples of the green colorant include C. I. Pigment Green (hereinafter, referred to as "PG") 7, PG10, PG36, PG37, PG58, and PG59, and in view of recognition of hemoglobin, it is preferable to contain at least one selected from the group consisting of PG7, PG36, and PG58.

The content of the green colorant is preferably 5 mass % to 60 mass % and more preferably 10 mass % to 40 mass % with respect to the total mass of the first composition.

[Orange Colorant]

As the orange colorant, a well-known colorant can be used without particular limitation, but an organic pigment is preferable.

Examples of the orange colorant include C. I. Pigment Orange (hereinafter, referred to as "POr") 2, POr5, POr13, POr16, POr17:1, POr31, POr34, POr36, POr38, POr43, POr46, POr48, POr49, POr51, POr52, POr55, POr59, POr60, POr61, POr62, POr64, POr71, and POr73, and in view of recognition of hemoglobin, it is preferable to contain at least one selected from the group consisting of POr71, POr36, POr38, POr43, POr62, and POr64.

The content of the orange colorant is preferably 5 mass % to 60 mass % and more preferably 10 mass % to 40 mass % with respect to the total mass of the first composition.

[Other Colorants]

The first composition according to the present embodiment may contain other colorants.

Examples of the other colorants include a blue colorant, a yellow colorant, a red colorant, but a yellow colorant is preferable.

As the other colorants, well-known colorants can be used without particular limitation, but an organic pigment is preferable.

Examples of the blue colorant include Pigment Blue (hereinafter, referred to as "PB") 1, PB15, PB15:1, PB15:2, PB15:3, PB15:4, PB15:6, PB16, PB17-1, PB22, PB27, PB28, PB29, PB36, and PB60.

Examples of the yellow colorant include Pigment Yellow (hereinafter, referred to as "PY") 1, PY3, PY12, PY13, PY14, PY17, PY34, PY35, PY37, PY55, PY74, PY81, PY83, PY93, PY94, PY95, PY97, PY108, PY109, PY110, PY120, PY137, PY138, PY139, PY150, PY153, PY154, PY155, PY157, PY166, PY167, PY168, PY180, PY185, and PY193.

Examples of the red colorant include Pigment Red (hereinafter, referred to as "PR") 3, PR5, PR9, PR19, PR22, PR31, PR38, PR42, PR43, PR48:1, PR48:2, PR48:3, PR48:4, PR48:5, PR49:1, PR53:1, PR57:1, PR57:2, PR58:4, PR63:1, PR81, PR81:1, PR81:2, PR81:3, PR81:4, PR88, PR104, PR108, PR112, PR122, PR123, PR144, PR146, PR149, PR166, PR168, PR169, PR170, PR177, PR178, PR179, PR184, PR185, PR208, PR216, PR224, PR226, PR254, PR257, PR264, Pigment Violet (hereinafter, referred to as "PV") 3, PV19, PV23, PV29, PV30, PV37, PV50, and PV88.

Among these, the other colorants preferably contain at least one colorant selected from the group consisting of PY139, PY150, and PY185.

[Preferable Aspect of Colorant]

In the first composition according to the present embodiment, the total content of the green colorant and the orange colorant are preferably 80 mass % or more, more preferably 90 mass % or more, and even more preferably 95 mass % or more with respect to the total mass of the colorant included in the composition. The upper limit of the total content is not particularly limited, and may be 100 mass % or less.

The mass ratio of the green colorant and the orange colorant (i.e., the green colorant : the orange colorant) is preferably from 70:30 to 30:70, more preferably from 65:45 to 45:65, and even more preferably from 60:40 to 40:60.

In view of recognition of hemoglobin, the first composition according to the present embodiment preferably contains at least one selected from the group consisting of PG7, PG36, and PG58, and at least one selected from the group consisting of POr71, POr36, POr38, POr43, POr62, and POr64, and more preferably further contains at least one colorant selected from the group consisting of PY139, PY150, and PY185.

All the combinations of these colorants are combinations of colorants having high absorbance and are preferable because similar waveforms can be obtained in the absorption spectrum of the composition. PG58, PG7, and PG36 are materials having absorption spectrums close to each other, POr38, POr43, POr62, and POr64 are materials having absorption spectrums close to each other, and PY139, PY150, and PY185 are materials having absorption spectrums close to each other.

<Alkali Soluble Resin>

The first composition preferably contains an alkali soluble resin. In a case where the first composition contains an alkali soluble resin, for example, development by an alkali aqueous solution can be performed, and thus it is possible to form a pattern by a composition.

In the present embodiment, the expression "alkali soluble" refers to being soluble in 1 mol/l of sodium hydroxide solution at 25° C.

The alkali soluble resin is not particularly limited except that the resin has alkali solubility, and can preferably be selected from in view of heat resistance, developability, availability, and the like.

It is preferable that the alkali soluble resin is a linear organic high molecular weight polymer, is soluble in an organic solvent, and can be developed with a weak alkali aqueous solution. The linear organic high molecular weight polymer is a polymer having carboxylic acid in a side chain, examples thereof include a methacrylic acid copolymer, an acrylic acid copolymer, an itaconic acid copolymer, a crotonic acid copolymer, a maleic acid copolymer, and a partially esterified maleic acid copolymer, as disclosed in JP1984-044615A (JP-S59-044615A), JP1979-034327B (JP-S54-034327B), JP1983-012577B (JP-S58-012577B), JP1979-025957B (JP-S54-025957B), JP1984-053836A (JP-S59-053836A), and JP59-71048A (JP-S59-071048A), and an acidic cellulose derivative similarly having carboxylic acid in a side chain thereof is useful.

In addition to those described above, as the alkali soluble resin, one obtained by adding an acid anhydride to a polymer having a hydroxyl group, a polyhydroxystyrene-based resin, a polysiloxane-based resin, a poly(2-hydroxyethyl (meth) acrylate), polyvinyl pyrrolidone, polyethylene oxide, and polyvinyl alcohol and the like are also useful. The linear organic high molecular weight polymer may be one obtained by copolymerizing a hydrophilic monomer. Examples of the linear organic high molecular weight polymer include alkoxyalkyl (meth)acrylate, hydroxyalkyl (meth)acrylate, glycerol (meth)acrylate, (meth)acrylamide, N-methylol acrylamide, secondary or tertiary alkyl acrylamide, dialkylaminoalkyl (meth)acrylate, morpholine (meth)acrylate, N-vinylpyrrolidone, N-vinylcaprolactam, vinylimidazole, vinyltriazole, methyl (meth)acrylate, ethyl (meth)acrylate, branched or linear propyl (meth)acrylate, branched or linear butyl (meth)acrylate, and phenoxyhydroxypropyl (meth) acrylate. As hydrophilic monomers, monomers including a tetrahydrofurfuryl group, a phosphoric acid group, a phosphoric acid ester group, a quaternary ammonium base, an ethylene oxy chain, a propylene oxy chain, a sulfonic acid group, a group derived from a salt thereof, a morpholinoethyl group and the like are also useful.

In order to improve the crosslinking efficiency, the alkali soluble resin may have a polymerizable group in a side chain, and for example, a polymer that contains an allyl group, a (meth)acrylic group, an allyloxyalkyl group, and the like in the side chain is also useful. As an alkali soluble resin having a polymerizable group, an alkali soluble resin that contains an allyl group, a (meth)acrylic group, an allyloxyalkyl group or the like in a side chain or the like is useful. Examples of the alkali soluble resin that contains a polymerizable group include DIANAL NR series (Mitsubishi Rayon Co., Ltd.), Photomer 6173 (COOH-containing polyurethane acrylic oligomer. manufactured by Diamond Shamrock Co. Ltd.), VISCOAT R-264 and KS RESIST 106 (all manufactured by Osaka Organic Chemical Industry Co., Ltd.), CYCLOMER P series and PLACCEL CF200 series (all manufactured by Daicel Corporation), and EBECRYL 3800 (manufactured by Daicel UBC Co., Ltd.).

In order to increase the strength of the cured film, alcohol-soluble nylon or polyether of 2,2-bis(4-hydroxyphenyl) propane and epichlorohydrin, or the like is also useful.

Among various kinds of alkali soluble resins, in view of heat resistance, a polyhydroxystyrene-based resin, a polysiloxane-based resin, an acrylic resin, an acrylamide-based resin, and an acrylic/acrylamide copolymer resin are preferable in view of heat resistance, and an acrylic resin, an acrylamide-based resin, and an acrylic/acrylamide copolymer resin are preferable in view of control of developability.

As an acrylic resin, a copolymer including monomers selected from benzyl (meth)acrylate, (meth)acrylic acid, hydroxyethyl (meth)acrylate, (meth)acrylamide, commercially available KS resist-106 (manufactured by Osaka Organic Chemical Industry Co., Ltd.), CYCLOMER P series (manufactured by Daicel Corporation), and the like are preferable.

In view of developability, liquid viscosity, and the like, the weight average molecular weight of the alkali soluble resin is preferably 1,000 to 200,000, more preferably 2,000 to 100,000, and even more preferably 5,000 to 50,000.

According to the present embodiment, the weight average molecular weight (Mw) means a value measured by gel permeation chromatography (GPC).

In the measurement of Mw by gel permeation chromatography (GPC), HLC (registered trademark)-8020 GPC (manufactured by Tosoh Corporation) is used as a determination device, and three items of TSKgel (registered trademark) Super Multipore HZ-H (4.6 mm ID×15 cm, manufactured by Tosoh Corporation) are used as columns, and THF (tetrahydrofuran) is used as an eluent. Measurement conditions are the sample concentration of 0.45 mass %, the flow rate of 0.35 ml/min, the sample injection amount of 10 μl, and the measurement temperature of 40° C., and the measurement is performed by using an RI detector.

The calibration curve is manufactured from eight samples of "Standard sample TSK standard, polystyrene" manufactured by Tosoh Corporation: "F-40", "F-20", "F-4", "F-1", "A-5000", "A-2500", "A-1000", and "n-propylbenzene".

The content of the alkali soluble resin is preferably 10 mass % to 80 mass % and more preferably 15 mass % to 60 mass % with respect to the total solid content of the composition. The alkali soluble resin may be used singly, and two or more kinds thereof may be used in combination.

The solid content according to the present disclosure refers to a total mass excluding a solvent from the composition.

<Polymerizable Compound and Polymerization Initiator>

The first composition preferably includes a polymerizable compound and a polymerization initiator and more preferably includes a polymerizable compound and a photopolymerization initiator.

In a case where the first composition includes a polymerizable compound and a polymerization initiator, it is possible to obtain a cured product by the first composition. In view of pattern forming, it is preferable to include an alkali soluble resin, a polymerizable compound, and a polymerization initiator.

(Polymerizable Compound)

The composition according to the first embodiment of the present invention preferably includes a polymerizable compound. The polymerizable compound can be used without particular limitation, as long as the polymerizable compound is a compound that is polymerizable by applying energy. Examples of the polymerizable compound include a radical polymerizable compound and a cation polymerizable compound, but the polymerizable compound is preferably a radical polymerizable compound and more preferably a compound having an ethylenically unsaturated group.

The polymerizable compound according to the embodiment is selected from a compound having at least one ethylenically unsaturated group and preferably a compound having two or more ethylenically unsaturated groups. The ethylenically unsaturated group is preferably a terminal ethylenically unsaturated group. Such a compound group is widely known in the relevant industrial field, and in the present embodiment, a well-known polymerizable compound can be used without particular limitation. The compound group may have a chemical form such as a monomer, a prepolymer, that is, a dimer, a trimer, and an oligomer, a mixture thereof, or a (co)polymer thereof.

Examples of the monomer and the (co)polymer thereof include an unsaturated carboxylic acid (for example, acrylic acid, methacrylic acid, itaconic acid, crotonic acid, isocrotonic acid, maleic acid), esters thereof, amide thereof, and a (co)polymer of the aforementioned components, and ester of unsaturated carboxylic acid and an aliphatic polyhydric alcohol compound, amide of unsaturated carboxylic acid and an aliphatic polyvalent amine compound, and a (co)polymer thereof are preferable.

An addition reaction product of unsaturated carboxylic acid ester or amide having a nucleophilic substituent such as a hydroxy group, an amino group, or a mercapto group with a monofunctional or polyfunctional isocyanate compound or an epoxy compound or a dehydration condensation reaction product with monofunctional or polyfunctional carboxylic acid is also preferably used. Unsaturated carboxylic acid ester or amides having an electrophilic substituent such as an isocyanate group or an epoxy group, an addition reaction product with monofunctional or polyfunctional alcohols, amines, or thiols, unsaturated carboxylic acid ester or amide having a releasable substituent such as a halogen group or a tosyloxy group, or a substitution reaction product with monofunctional or polyfunctional alcohol, amine, or thiol is also appropriate. As another example, instead of the unsaturated carboxylic acid, a compound group substituted with unsaturated phosphonic acid or styrene, vinyl ether, or the like may be used.

With respect to the polymerizable compound, details of a usage method such as the structure of the polymerizable compound, either of the single use or the combination use of two or more, or the content of the polymerizable compound can be appropriately set according to the final performance design of the composition.

For example, in view of sensitivity, a structure in which a content of the unsaturated groups per molecule is high is preferable, and a bifunctional or higher functional group is preferable in many cases. In view of increasing the strength of the coloring agent-containing layer, a trifunctional or higher functional compound, for example, a hexafunctional acrylate compound can be used.

A method of adjusting both of the sensitivity and the strength by using a compound having a different functional number or another polymerizable group, for example, acrylic acid ester, methacrylic acid ester, a styrene-based compound, and a vinyl ether-based compound in combination is available.

As the polymerizable compound, a commercially available compound may be used. Examples of the commercially available compound include KAYARAD (registered trademark) PET-30 and KAYARAD TPA-330 manufactured by Nippon Kayaku Co., Ltd., POLYVEST (registered trademark) 110M manufactured by Evonik Industries AG, and polyfunctional acrylate A-9300 (trade name) manufactured by Shin-Nakamura Chemical Co., Ltd.

The polymerizable compound may be contained singly in the first composition, or two or more kinds thereof may be used in combination.

The content of the polymerizable compound in the first composition is not particularly limited. For example, the content of the polymerizable compound is preferably 30 mass % to 99.5 mass %, more preferably 50 mass % to 99 mass %, and even more preferably 60 mass % to 98 mass % with respect to the total solid content in the composition.

A preferable aspect in a case where a polymer compound is used as the polymerizable compound is provided below.

Examples of the polymerizable compound (hereinafter, referred to as a "curable resin") that is a high molecular weight compound include a (meth)acrylic resin having a polymerizable group, a polyester resin, a urethane resin, and a fluorine-based resin.

In the present embodiment, even in a case where an alkali soluble resin has a polymerizable group, the alkali soluble resin is not included in the polymerizable compound but is included in the alkali soluble resin.

The curable resin in the first composition may be used singly or two or more kinds thereof may be used in combination. In view of the film uniformity, it is preferable to use the curable resin singly.

In view of the strength of the coloring agent-containing layer, it is preferable that the curable resin has a crosslinking structure. The method of forming a crosslinking structure in the curable resin is not particularly limited. Examples thereof include a method of using a polyfunctional (meth)acrylate monomer that can be combined with a reaction group included in the curable resin and a method of introducing a reactive group (for example, a hydroxy group) into a (meth)acrylic resin as a curable resin and causing the (meth)acrylic resin to react with a crosslinking agent which reacts with the reactive group.

Specific examples of the method of introducing the reactive group into the (meth)acrylic resin include a method of causing a (meth)acrylic resin including a structural unit derived from a (meth)acrylate monomer having a group including one or more kinds of active hydrogen, which is selected from the group consisting of a hydroxy group, a primary amino group, and a secondary amino group with an isocyanate group-containing crosslinking agent, that is, a compound having two or more isocyanate groups in one molecule. In a case where the (meth)acrylate resin having a reactive group is synthesized, it is preferable that three or more polyfunctional (meth)acrylate monomers are used, since the crosslinking density of the obtained coloring agent-containing layer is increased, and the strength is further improved.

As the crosslinking agent, it is possible to appropriately use the well-known crosslinking agent. Examples of the crosslinking agent used in the present embodiment include AD-TMP and A-9550 (all are trade names) manufactured by Shin-Nakamura Chemical Co., Ltd.

The content of the curable resin is not particularly limited, and is preferably 30 mass % to 99.5 mass %, more preferably 50 mass % to 99 mass %, and even more preferably 60 mass % to 98 mass % with respect to the total solid content of the first composition.

The content of the crosslinking agent to be used in combination with the curable resin is preferably 5 parts by mass to 80 parts by mass and more preferably 10 parts by mass to 50 parts by mass with respect to 100 parts by mass of the curable resin.

[Polymerization Initiator]

The polymerization initiator is not particularly limited as long as the polymerization initiator is a compound that can generate initiating species that are required for the polymerization by applying energy, and the polymerization initiator can be appropriately selected from well-known photopolymerization initiators and thermal polymerization initiators, and the polymerization initiator is preferably a photopolymerization initiator because the binder can be formed easily.

For example, the photopolymerization initiator is preferably an initiator having photosensitivity to visible rays from the ultraviolet region, may be an activator which generates some action with the photosensitized sensitizing agent to generate active radicals, or may be an initiator which initiates cationic polymerization according to the type of monomer.

Examples of the photopolymerization initiator include a halogenated hydrocarbon derivative such as a photopolymerization initiator having a triazine skeleton or a photopolymerization initiator having an oxadiazole skeleton, an acylphosphine compound such as acylphosphine oxide, an oxime compound such as hexaarylbiimidazole and an oxime derivative, organic peroxide, a thio compound, a ketone compound, aromatic onium salt, keto oxime ether, an aminoacetophenone compound, and hydroxyacetophenone. As the aminoacetophenone-based initiator, compounds disclosed in JP2009-191179A, of which the absorption wavelength is adjusted for a long wave light source of 365 nm, 405 nm, or the like, can also be used.

For example, an aminoacetophenone-based initiator disclosed in JP1998-291969A (JPH10-291969A) and an acylphosphine oxide-based initiator disclosed in JP4225898B can be used.

As the photopolymerization initiator, a synthesized product may be used, or a commercially available compound may be used. As the commercially available compound used in the present embodiment, examples of the hydroxyacetophenone initiator include IRGACURE (registered trademark)-184, DAROCUR (registered trademark)-1173, IRGACURE-500, IRGACURE-2959, and IRGACURE-127 (trade name: all are manufactured by BASF SE).

Examples of the aminoacetophenone-based initiator include IRGACURE-907, IRGACURE-369, and IRGACURE-379 (trade name: all are manufactured by BASF SE).

Examples of the acylphosphine type initiator include IRGACURE-819 and DAROCUR-TPO (trade name: all are manufactured by BASF SE).

As the photopolymerization initiator, an oxime-based compound is more preferable. Specific examples of the oxime-based compound include compounds disclosed in JP2001-233842A, compounds disclosed in JP2000-80068A, compounds disclosed in JP2006-342166A, and compound disclosed in paragraphs 0073 to 0075 of JP2016-6475A.

Examples of the commercially available compound of the oxime ester compound that can be used as the photopolymerization initiator according to the embodiment include IRGACURE-OXE01 (manufactured by BASF SE) and IRGACURE-OXE02 (manufactured by BASF SE).

Examples of the cation polymerization initiator which is an initiator that initiates cation polymerization include well-known compounds such as a photoinitiator for photo cationic polymerization, a photo-decoloring agent based on coloring agents, a photochromic agent, and known acid generators that are used in a micro resist or the like, and a mixture thereof.

Examples of the cation polymerization initiator that can be used in the present embodiment include an onium compound, an organic halogen compound, or a disulfone compound. Specific examples of the organic halogen compound and the disulfone compound include compounds as described for the compound generating radicals.

Examples of the onium compound include diazonium salt, ammonium salt, iminium salt, phosphonium salt, iodonium salt, sulfonium salt, arsonium salt, and selenonium salt, and examples thereof include the compounds disclosed in paragraphs 0058 to 0059 of JP2002-29162A.

In the first component, the polymerization initiator may be used singly, or two or more kinds thereof may be used in combination.

The content of the polymerization initiator is preferably 0.1 mass % to 20 mass %, more preferably 0.3 mass % to 15 mass %, and even more preferably 0.4 mass % to 10 mass % with respect to the total solid content of the first composition.

<Other Components>

The first composition may contain other components. Examples of other components include a solvent, a surfactant, a filler, an antioxidant, an ultraviolet absorbing agent, an aggregation inhibitor, a sensitizer, and a light stabilizer.

[Surfactant]

The first composition may include a surfactant.

The surfactant may be any of nonionic, cationic or anionic surfactants, and a fluorine-containing surfactant is preferable. Specific examples thereof include surfactants disclosed in JP1990-054202A (JP-H02-054202A).

The content of the surfactant is preferably 0.0001 mass % to 1 mass % with respect to the total solid content of the composition.

[Solvent]

The first composition may contain a solvent.

As the solvent, well-known solvents can be used without particular limitation, and it is preferable that the solvent is selected in consideration of, for example, the solubility of other components included in the first composition, the coatability of the composition, safety, or the like.

As the solvent, esters, ethers, ketones, and aromatic hydrocarbons are used, and examples thereof include those disclosed in paragraphs 0161 and 0162 of JP2012-032754A.

The content of the solvent is preferably an amount in which the total solid content of the first composition becomes 10 mass % to 80 mass % and preferably an amount in which the total solid content becomes 15 mass % to 60 mass %.

<Method of Preparing First Composition>

The first composition is prepared by mixing each of the components described above with an optional component, if necessary.

In a case of preparing the first composition, the respective components constituting the first composition are collectively formulated, or sequentially formulated after the respective components are dissolved or dispersed in a solvent. The order of introduction and the working conditions for formulation are not particularly limited. All components may be simultaneously dissolved and dispersed in a solvent to prepare a composition, and, if necessary, in two or more solutions or dispersion liquids, respective components are appropriately are mixed in a case of usage (for example, at a case of application) to be prepared as the composition.

The first composition prepared as described above can be provided for usage after being separated by filtration with a filter preferably having a pore size of 0.01 μm to 3.0 μm and more preferably having a pore size of 0.05 μm to 0.5 μm.

(Second Composition)

With respect to the second composition according to the present embodiment, in a case where the absorbance at 500 nm is $A_{500}$, the absorbance at 580 nm is $B_{580}$, the absorbance at 600 nm is $C_{600}$, $B_{580}/A_{500}$ is 5.0 or more, and $C_{600}/A_{500}$ is 5.0 or more.

The second composition is preferably a photosensitive composition and is more preferably a negative photosensitive composition in view of forming a color filter.

The second composition is preferably for manufacturing a color filter.

<Absorbance and Minimum Absorption Wavelength>

In view of recognition of hemoglobin, $B_{580}/A_{500}$ is 5.0 or more, preferably 6.0 to 10,000, and more preferably 7.0 to 10,000.

In view of recognition of hemoglobin, $C_{600}/A_{500}$ is 5.0 or more, preferably 7.0 to 10,000, and more preferably 9.0 to 10,000.

In a case where the absorbance at 450 nm is $E_{450}$, $E_{450}/A_{500}$ is preferably 5.0 or more, more preferably 7.0 to 10,000, and even more preferably 9.0 to 10,000.

In view of recognition of hemoglobin, $A_{500}$ is preferably 0.003 to 0.5, more preferably 0.003 to 0.4, and even more preferably 0.003 to 0.3.

$B_{580}/A_{500}$, $C_{600}/A_{500}$, $E_{450}/A_{500}$, and $A_{500}$ are adjusted by the kinds and the contents of the colorant contained in the composition.

In view of recognition of hemoglobin, in the second composition, the minimum absorption wavelength in the wavelength range of 400 nm to 700 nm is preferably present in the range of 480 nm to 520 nm, more preferably present in the range of 485 nm to 515 nm, and even more preferably present in the range of 490 nm to 510 nm.

The absorbance at the minimum absorption wavelength is preferably 0.4 or less, more preferably 0.3 or less, and even more preferably 0.25 or less.

The lower limit of the absorbance is not particularly limited and may be 0 or more.

<Colorant>

The second composition according to the present embodiment preferably contains a blue colorant and a yellow colorant. In a case where a blue colorant and a yellow colorant are contained, it is possible to easily obtain a composition having $B_{580}/A_{500}$ of 5.0 or more, and $C_{600}/A_{500}$ of 5.0 or more.

Details of each of the colorants are described.

[Blue Colorant]

As the blue colorant, a well-known colorant can be used without particular limitation, but an organic pigment is preferable.

Examples of the blue colorant include PB1, PB2, PB3, PB15, PB15:1, PB15:2, PB15:3, PB15:4, PB15:6, PB16, PB17-1, PB22, PB27, PB28, PB29, PB36, and PB60, and in view of recognition of hemoglobin, PB15:6 is preferably contained.

The content of the blue colorant is preferably 1 mass % to 50 mass % and more preferably 10 mass % to 30 mass % with respect to the total mass of the second composition.

[Yellow Colorant]

As the yellow colorant, a well-known colorant can be used without particular limitation, but an organic pigment is preferable.

Examples of the yellow colorant include PY1, PY3, PY12, PY13, PY14, PY17, PY34, PY35, PY37, PY55, PY74, PY81, PY83, PY93, PY94, PY95, PY97, PY108, PY109, PY110, PY120, PY137, PY138, PY139, PY150, PY153, PY154, PY155, PY157, PY166, PY167, PY168, PY180, PY185, and PY193, and in view of recognition of hemoglobin, at least one selected from the group consisting of PY139, PY150, and PY185 is preferably contained.

The content of the yellow colorant is preferably 1 mass % to 50 mass % and more preferably 10 mass % to 30 mass % with respect to the total mass of the second composition.

[Other Colorants]

The second composition according to the present embodiment may contain other colorants.

Examples of the other colorants include a green colorant, an orange colorant, and a red colorant, and a red colorant is preferable.

Examples of the green colorant and the orange colorant include a green colorant and an orange colorant used in the above first composition.

Examples of the red colorant include PR3, PR5, PR9, PR19, PR22, PR31, PR38, PR42, PR43, PR48:1, PR48:2, PR48:3, PR48:4, PR48:5, PR49:1, PR53:1, PR57:1, PR57:2, PR58:4, PR63:1, PR81, PR81:1, PR81:2, PR81:3, PR81:4, PR88, PR104, PR108, PR112, PR122, PR123, PR144, PR146, PR149, PR166, PR168, PR169, PR170, PR177, PR178, PR179, PR184, PR185, PR208, PR216, PR226, PR257, Pigment Violet (hereinafter, referred to as "PV") 3, PV19, PV23, PV29, PV30, PV37, PV50, PV88, a pyrromethene dye, and an xanthene dye.

Among these, it is preferable that the other colorants contain at least one colorant selected from the group consisting of PV23, a pyrromethene dye, and a xanthene dye.

[Preferable Aspect of Colorant]

In the second composition according to the present embodiment, the total content of the blue colorant and the yellow colorant is preferably 80 mass % or more, more preferably 90 mass % or more, and even more preferably 95 mass % or more with respect to the total mass of the colorant included in the composition.

The upper limit value of the total content is not particularly limited, and may be 100% by mass or less.

The mass ratio of the blue colorant and the yellow colorant is preferably the blue colorant: the yellow colorant=70:30 to 30:70, more preferably 65:45 to 45:65, and even more preferably 40:60 to 60:40.

In view of recognition of hemoglobin, the second composition according to the present embodiment is preferably contains at least one colorant selected from the group consisting of PB15:6, PY139, PY150, and PY185, and may further contain at least one colorant selected from the group consisting of PV23, a pyrromethene dye, and a xanthene dye.

All the combinations of these colorants are combinations of colorants having high absorbance and are preferable because similar waveforms can be obtained in the absorption spectrum of the composition. PY139, PY150, and PY185 are materials having absorption spectrums close to each other, and PV23, a pyrromethene dye, and a xanthene dye are materials having absorption spectrums close to each other.

<Alkali Soluble Resin, Polymerizable Compound, and Polymerization Initiator>

The second composition preferably contains an alkali soluble resin. In a case where the second composition contains an alkali soluble resin, for example, development by an alkali aqueous solution can be performed, and thus it is possible to form a pattern by a composition.

The second composition preferably includes a polymerizable compound and a polymerization initiator and more preferably includes a polymerizable compound and a photopolymerization initiator.

In a case where the second composition includes a polymerizable compound and a polymerization initiator, the pattern can be formed by the second composition. In view of pattern forming, it is preferable to include an alkali soluble resin, a polymerizable compound, and a polymerization initiator.

The alkali soluble resin, the polymerizable compound, and the polymerization initiator according to the second composition are the same as the alkali soluble resin, the polymerizable compound, and the polymerization initiator included in the first composition, and the preferable aspect is also the same.

<Other Components>

The second composition may contain other components. The components according to the second composition are the same as the other components according to the first composition, and the preferable aspect thereof is also the same.

<Method of Preparing Second Composition>

The method of preparing a second composition is the same as the method of preparing a first composition, and a preferable aspect thereof is also the same.

(Color Filter)

The color filter according to the present embodiment is preferably a color filter in which the first composition according to the present embodiment or the second composition according to the present embodiment is used, and more preferably a color filter that includes a cured product of the first composition according to the present embodiment or a cured product of the second composition according to the present embodiment.

The color filter according to the present embodiment may be a color filter having a plurality of pixels and is more preferably a color filter having at least two pixels selected from the group consisting of a color filter 1 in which, in a case where an absorbance at 500 nm is $A_{500}$, an absorbance at 580 nm is $B_{580}$, an absorbance at 600 nm is $C_{600}$, and an absorbance at 540 nm is $D_{540}$, $A_{500}/B_{580}$ is 2.0 or more, and $C_{600}/B_{580}$ is 1.5 or more, a color filter 2 in which $B_{580}/A_{500}$ is 5.0 or more, and $C_{600}/A_{500}$ is 5.0 or more, a color filter 3 in which $A_{500}/D_{540}$ is 1.5 or more, and $C_{600}/D_{540}$ is 3.0 or more, and a color filter 4 in which $A_{500}/C_{600}$ is 5.0 or more, and $B_{580}/C_{600}$ is 3.0 or more, and at least having the color filter 1 or the color filter 2.

With respect to the absorbance and the minimum absorption wavelength of the color filter, an absorbance in a visible light region at a wavelength of 400 nm to 700 nm is obtained by using a spectrophotometer of an ultraviolet visible near infrared spectrophotometer U-4150 (manufactured by Hitachi High-Technologies Corporation). The absorbance is a value obtained by subtracting the absorbance of only the glass substrate which is not coated with the composition as a reference value (reference).

<Color Filter 1>

The color filter 1 preferably contains a green colorant and an orange colorant. The kinds, the contents, the combination of the preferable kinds, and the preferable content ratio of the green colorant and the orange colorant are the same as those of the green colorant and the orange colorant in the first composition, and the preferable aspect thereof is also the same.

The color filter 1 may contain other colorants. The other colorants are the same as the other colorants in the first composition, and the preferable aspect thereof is also the same.

In view of recognition of hemoglobin, $A_{500}/B_{580}$ is 2.0 or more, preferably 2.0 to 10,000, and more preferably 3.0 to 10,000.

In view of recognition of hemoglobin, $C_{600}/B_{580}$ is 1.5 or more, preferably 1.5 to 10,000, and more preferably 1.6 to 10,000.

In view of recognition of hemoglobin, $B_{580}$ is preferably 0.003 to 0.5, more preferably 0.003 to 0.4, and even more preferably 0.003 to 0.3.

$A_{500}/B_{580}$, $C_{600}/B_{580}$, and $B_{580}$ are adjusted according to the kinds and the contents of the colorant contained in the color filter.

In view of recognition of hemoglobin, the minimum absorption wavelength of the color filter 1 in the wavelength range of 400 nm to 700 nm is preferably present in the range of 565 nm to 595 nm, more preferably present in the range of 570 nm to 590 nm, and even more preferably present in the range of 575 nm to 585 nm.

The absorbance at the minimum absorption wavelength is preferably 0.4 or less, more preferably 0.3 or less, and even more preferably 0.25 or less.

The lower limit of the absorbance is not particularly limited, and may be 0 or more.

<Color Filter 2>

The color filter 2 preferably contains a blue colorant and a yellow colorant.

The kinds, the contents, the combination of the preferable kinds, and the preferable content ratio of the blue colorant and the yellow colorant are the same as those of the blue colorant and the yellow colorant in the first composition, and the preferable aspect thereof is also the same.

The color filter 2 may contain other colorants. The other colorants are the same as the other colorants in the second composition, and the preferable aspect thereof is also the same.

In view of recognition of hemoglobin, $B_{580}/A_{500}$ is 5.0 or more, preferably 6.0 to 10,000, and more preferably 7.0 to 10,000.

In view of recognition of hemoglobin, $C_{600}/A_{500}$ is 5.0 or more, preferably 7.0 to 10,000, and more preferably 9.0 to 10,000.

$E_{450}/A_{500}$ in a case where the absorbance at 450 nm is $E_{450}$ is preferably 5.0 or more, more preferably 7.0 to 10,000, and even more preferably 9.0 to 10,000.

In view of recognition of hemoglobin, $A_{500}$ is preferably 0.003 to 0.5, more preferably 0.003 to 0.4, and even more preferably 0.003 to 0.3.

$B_{580}/A_{500}$, $C_{600}/A_{500}$, $E_{450}/A_{500}$, and $A_{500}$ are adjusted according to the kind and the content of the colorant contained in the composition.

In view of recognition of hemoglobin, the minimum absorption wavelength at a wavelength range of 400 nm to 700 nm in the color filter 2 is preferably present in the range of 480 nm to 520 nm, more preferably present in the range of 485 nm to 515 nm, and even more preferably present in the range of 490 nm to 510 nm.

The absorbance in the minimum absorption wavelength is preferably 0.4 or less, more preferably 0.3 or less, and even more preferably 0.25 or less.

The lower limit of the absorbance is not particularly limited, and may be 0 or more.

<Color Filter 3>

The color filter 3 preferably contains a green colorant.

The kinds and the content of the green colorant are the same as the kind and the content of the green colorant in a third composition, and the preferable aspect is also the same.

The color filter 3 may contain other colorants. The other colorants are the same as the other colorants in the third composition, and the preferable aspect thereof is also the same.

In view of recognition of hemoglobin, $A_{500}/D_{540}$ is 1.5 or more, preferably 1.6 to 10,000, and more preferably 1.7 to 10,000.

In view of recognition of hemoglobin, $C_{600}/D_{540}$ is 3.0 or more, preferably 4.0 to 10,000, and more preferably 5.0 to 10,000.

In view of recognition of hemoglobin, $D_{540}$ is preferably 0.03 to 0.5, more preferably 0.03 to 0.3, and even more preferably 0.03 to 0.2.

In view of recognition of hemoglobin, the minimum absorption wavelength of the color filter 3 in the wavelength range of 400 nm to 700 nm is preferably present in the range of 520 nm to 560 nm, more preferably present in the range of 525 nm to 555 nm, and even more preferably present in the range of 530 nm to 550 nm.

The absorbance at the minimum absorption wavelength is preferably 0.4 or less, more preferably 0.3 or less, and even more preferably 0.25 or less.

The lower limit of the absorbance is not particularly limited, and may be 0 or more.

<Color Filter 4>

The color filter 4 preferably contains an orange colorant or a red colorant.

The kind and the content of the orange colorant and the red colorant are the same as those of the orange colorant and the red colorant in a fourth composition, and the preferable aspect thereof is also the same.

The color filter 4 may contain the other colorant. The other colorants are the same as the other colorants in the fourth composition, and the preferable aspect thereof is also the same.

In view of recognition of hemoglobin, $A_{500}/C_{600}$ is 5.0 or more, preferably 7.0 to 10,000, and more preferably 8.0 to 10,000.

In view of recognition of hemoglobin, $B_{580}/C_{600}$ is 3.0 or more, preferably 4.0 to 10,000, and more preferably 5.0 to 10,000.

$F_{650}/C_{600}$ は, in a case where the absorbance at 650 nm is $F_{650}$ is preferably 0.1 or more, more preferably 0.1 to 10,000, and even more preferably 0.15 to 10,000.

In view of recognition of hemoglobin, $C_{600}$ is preferably 0.003 to 0.5, more preferably 0.003 to 0.4, and even more preferably 0.003 to 0.3.

In view of recognition of hemoglobin, the minimum absorption wavelength of the color filter 4 in a wavelength range of 400 nm to 700 nm is preferably present in the range of 580 nm to 700 nm, more preferably present in the range of 585 nm to 700 nm, and even more preferably present in the range of 590 nm to 700 nm.

The absorbance in the minimum absorption wavelength is preferably 0.4 or less, more preferably 0.3 or less, and even more preferably 0.25 or less.

The lower limit of the absorbance is not particularly limited, and may be 0 or more.

As described above, it is known that the absorption wavelength of the hemoglobin in the range of visible light (400 nm to 700 nm) varies due to the difference in a valence of included iron, the binding ligand, or the like.

For example, oxygenated hemoglobin has maximum absorption wavelengths at around 540 nm and 580 nm, and thus has weak absorption of light at a wavelength around 500 nm. Deoxygenated hemoglobin has a maximum absorption wavelength at around 560 nm and has weak absorption of light at wavelengths around 540 nm and 580 nm. In addition, an equal absorption point of oxygenated hemoglobin and deoxygenated hemoglobin is present around 506 nm. Therefore, it is considered that, in a case where either or both of the color filter 1 and the color filter 2 are used, recognition of oxygenated hemoglobin by visible light becomes possible.

In addition to the color filter 1 and the color filter 2, in a case where a color filter further having the color filter 3 as a pixel is used, it is considered that the recognition of oxygenated hemoglobin by the visible light is excellent.

For example, since cyanmethemoglobin has a maximum absorption wavelength at around 540 nm, and has weak absorption of light at around 500 nm and around 580 nm, in a case where the above color filter further having the color filter 3 as a pixel is used, it is considered that cyanmethemoglobin can be specifically recognized by visible light or oxygenated hemoglobin and cyanmethemoglobin can be identified.

It is known that, regardless of a valence of included iron, the binding ligand, or the like, in most states, hemoglobin has weak absorption of light at around 600 nm.

Therefore, in addition to the color filter 1 and the color filter 2 (which may further have the color filter 3), in a case where a color filter further having the color filter 4 as a pixel is used, the influence of background due to a body tissue or other blood components can be removed, and thus it is considered that the recognition of hemoglobin is more excellent.

The color filter according to the present embodiment is preferably a color filter having a cured product of a composition on a support.

The color filter 1 is preferably a color filter using the above first composition, and more preferably a color filter having a cured product of the first composition on the support.

The color filter 2 is preferably a color filter using the above second composition and is more preferably a color filter having a cured product of the support.

The color filter 3 is preferably a color filter using the third composition and more preferably a color filter having a cured product of the third composition on the support.

The color filter 4 is preferably a color filter using the fourth composition and more preferably a color filter having a cured product of the fourth composition on the support.

<Support>

Examples of the support include glass and a photoelectric conversion element substrate such as a silicon substrate and a plastic substrate. In addition, on these supports, a black matrix for separating each pixel may be formed, or a transparent resin layer may be provided for promoting adhesion or the like. In addition, if necessary, on the support, an undercoat layer may be provided in order to improve the adhesion to an upper layer, to prevent the diffusion of substances, or to planarize the surface. The plastic substrate preferably further has at least one layer selected from a gas barrier layer and a solvent resistant layer on the surface thereof.

[Third Composition]

The third composition preferably contains a green colorant.

In the third composition, it is preferable that $A_{500}/D_{540}$ is 1.5 or more, and $C_{600}/D_{540}$ is 3.0 or more.

The third composition is preferably a photosensitive composition and more preferably a negative photosensitive composition in view of forming a color filter.

The third composition is preferably for manufacturing a color filter.

[Absorbance and Minimum Absorption Wavelength]

In view of recognition of hemoglobin, $A_{500}/D_{540}$ is 1.5 or more, preferably 1.6 to 10,000, and more preferably 1.7 to 10,000.

In view of recognition of hemoglobin, $C_{600}/D_{540}$ is 3.0 or more, preferably 4.0 to 10,000, and more preferably 5.0 to 10,000.

In view of recognition of hemoglobin, $D_{540}$ is preferably 0.03 to 0.5, more preferably 0.03 to 0.3, and even more preferably 0.03 to 0.2.

$A_{500}/D_{540}$, $C_{600}/D_{540}$, and $D_{540}$ are adjusted according to the kind and the content of the colorant contained in the composition.

According to the third composition, in view of recognition of hemoglobin, the minimum absorption wavelength in a wavelength range of 400 nm to 700 nm is preferably present in the range of 520 nm to 560 nm, more preferably present in the range of 525 nm to 555 nm, and even more preferably present in the range of 530 nm to 550 nm.

The absorbance in the minimum absorption wavelength is preferably 0.4 or less, more preferably 0.3 or less, and even more preferably 0.25 or less.

The lower limit of the absorbance is not particularly limited, and may be 0 or more.

[Colorant]

The third composition according to the present embodiment preferably contains a green colorant. In a case where containing a green colorant, it is possible to obtain a composition having $A_{500}/D_{540}$ of 1.5 or more and $C_{600}/D_{540}$ of 3.0 or more.

Details of each of the colorants are described.

—Green Colorant—

As the green colorant, a well-known colorant can be used without particular limitation, but an organic pigment is preferable.

The green colorant is the same as the green colorant according to the first composition, and the preferable aspect thereof is also the same.

—Other Colorants—

The third composition according to the present embodiment may contain other colorants.

Examples of the colorant include a blue colorant, a yellow colorant, an orange colorant, and a red colorant.

Examples of the blue colorant include the blue colorant used in the second composition.

Examples of the orange colorant and the red colorant include the orange colorant and the red colorant used in the first composition.

As the yellow colorant, a well-known colorant can be used without particular limitation, but an organic pigment is preferable.

Examples of the yellow colorant include PY1, PY3, PY12, PY13, PY14, PY17, PY34, PY35, PY37, PY55, PY74, PY81, PY83, PY93, PY94, PY95, PY97, PY108, PY109, PY110, PY120, PY137, PY138, PY139, PY150, PY153, PY154, PY155, PY157, PY166, PY167, PY168, PY180, PY185, and PY193, and in view of recognition of hemoglobin, it is preferable to contain at least one selected from the group consisting of PY139, PY150, and PY185.

—Preferable Aspect of Colorant—

In view of recognition of hemoglobin, the third composition according to the present embodiment preferably contains at least one colorant selected from the group consisting of PG7, PG36, and PG58, and may further contain at least one colorant selected from the group consisting of PY139, PY150, and PY185.

[Alkali Soluble Resin, Polymerizable Compound, Polymerization Initiator, other Components, and Method of Preparing Third Composition]

The third composition may contain an alkali soluble resin, a polymerizable compound, a polymerization initiator, and other components. The above components are the same as the respective components according to the first composition, and preferable aspects are also the same.

That is, except that the colorants are different, the third composition can have the same formulation as the first composition, and the preferable aspect thereof is also the same.

The method of preparing the third composition is the same as the method of preparing the first composition, and the preferable aspect thereof is also the same.

<Fourth Composition>

The fourth composition preferably contains an orange colorant or a red colorant. In the fourth composition, it is preferable that $A_{500}/C_{600}$ is 5.0 or more, and $B_{580}/C_{600}$ is 3.0 or more.

The fourth composition is preferably a photosensitive composition, and more preferably a negative photosensitive composition in view of forming a color filter.

The fourth composition is preferably for manufacturing a color filter.

[Absorbance and minimum absorption wavelength]

In view of recognition of hemoglobin, $A_{500}/C_{600}$ is 5.0 or more, preferably 7.0 to 10,000, and more preferably 8.0 to 10,000.

In view of recognition of hemoglobin, $B_{580}/C_{600}$ is 3.0 or more, preferably 4.0 to 10,000, and more preferably 5.0 to 10,000.

$F_{650}/C_{600}$ in a case where the absorbance at 650 nm is $F_{650}$ is preferably 0.1 or more, more preferably 0.1 to 10,000, and even more preferably 0.15 to 10,000.

In view of recognition of hemoglobin, $C_{600}$ is preferably 0.003 to 0.5, more preferably 0.003 to 0.4, and even more preferably 0.003 to 0.3.

$A_{500}/C_{600}$, $B_{580}/C_{600}$, $F_{650}/C_{600}$, and $C_{600}$ are adjusted according to the kind and the content of the colorant contained in the composition.

In view of recognition of hemoglobin, the minimum absorption wavelength of the fourth composition in the wavelength range of 400 nm to 700 nm is preferably present in the range of 580 nm to 700 nm, more preferably present in the range of 585 nm to 700 nm, and even more preferably present in the range of 590 nm to 700 nm.

The absorbance at the minimum absorption wavelength is preferably 0.4 or less, more preferably 0.3 or less, and even more preferably 0.25 or less.

The lower limit of the absorbance is not particularly limited, and may be 0 or more.

[Colorant]

The fourth composition according to the present embodiment preferably contains an orange colorant or a red colorant. In a case where an orange colorant or a yellow colorant is contained, it is possible to easily obtain a composition having $A_{500}/C_{600}$ of 5.0 or more, and $B_{580}/C_{600}$ of 3.0 or more.

Details of each of the colorants are described.

—Orange Colorant or Red Colorant—

As the orange colorant or the red colorant, a well-known colorant can be used without particular limitation, but an organic pigment is preferable.

Examples of the orange colorant include POr2, POr5, POr13, POr16, POr17:1, POr31, POr34, POr36, POr38, POr43, POr46, POr48, POr49, POr51, POr52, POr55, POr59, POr60, POr61, POr62, POr64, POr71, or POr73.

Examples of the red colorant include PR3, PR5, PR9, PR19, PR22, PR31, PR38, PR42, PR43, PR48:1, PR48:2, PR48:3, PR48:4, PR48:5, PR49:1, PR53:1, PR57:1, PR57:2, PR58:4, PR63:1, PR81, PR81:1, PR81:2, PR81:3, PR81:4, PR88, PR104, PR108, PR112, PR122, PR123, PR144, PR146, PR149, PR166, PR168, PR169, PR170, PR177, PR178, PR179, PR184, PR185, PR208, PR216, PR226, PR254, PR257, PR264, Pigment Violet (hereinafter, referred to as "PV") 3, PV19, PV23, PV29, PV30, PV37, PV50, and PV88.

Among these, it is preferable to include at least one colorant selected from the group consisting of PR254, PR264, and PR177.

—Other Colorants—

The fourth composition according to the present embodiment may contain other colorants.

Examples of the colorant include a blue colorant, a yellow colorant, and a green colorant.

Examples of the blue colorant include a blue colorant used in the above second composition.

Examples of the yellow colorant include PY1, PY3, PY12, PY13, PY14, PY17, PY34, PY35, PY37, PY55, PY74, PY81, PY83, PY93, PY94, PY95, PY97, PY108, PY109, PY110, PY120, PY137, PY138, PY139, PY150, PY153, PY154, PY155, PY157, PY166, PY167, PY168, PY180, PY185, and PY193, and in view of recognition of hemoglobin, it is preferable to contain at least one selected from the group consisting of PY139, PY150, and PY185.

Examples of the green colorant include a green colorant used in the above first composition.

—Preferable Aspect of Colorant—

In view of recognition of hemoglobin, the fourth composition according to the present embodiment preferably contains at least one colorant selected from the group consisting of PR254, PR264, and PR177, and may further contain at least one colorant selected from the group consisting of PY139, PY150, and PY185.

[Alkali Soluble Resin, Polymerizable Compound, Polymerization Initiator, other Components, and Method of Preparing Third Composition]

The fourth composition may contain an alkali soluble resin, a polymerizable compound, a polymerization initiator, and other components. The components are the same as the respective components according to the first composition, and the preferable aspects are also the same.

That is, except that the colorants are different, the fourth composition can have the same formulation as the first composition.

The method of preparing the fourth composition is the same as the method of preparing the first composition, and the preferable aspect is also the same.

<Method of Manufacturing Color Filter>

The color filter according to the present embodiment is not particularly limited, but can be appropriately manufactured by a manufacturing method including a step (coloration film forming step) of applying a composition on a support to form a coloration film and a step (coloration pattern forming step) of exposing the coloration film in a pattern shape to form a coloration cured film in pattern shape by development.

The composition may be any one of the first composition, the second composition, the third composition, and the fourth composition, and another composition may be further used, but it is preferable to apply at least any one of the first composition and the second composition, and it is more preferable that the first composition and the second composition are respectively applied to other compartments separated by a black matrix or the like.

[Composition for Forming Black Matrix]

For example, the black matrix is manufactured by using the composition for forming a black matrix.

The composition for forming a black matrix is a composition containing a black colorant.

Examples of the black colorant include carbon black, titanium carbon, iron oxide, titanium oxide, and graphite, and among these, carbon black is preferable.

The composition for forming a black matrix may contain an alkali soluble resin, a polymerizable compound, a polymerization initiator, and other components. The respective components are the same as the respective components in the first composition, and a preferable aspect thereof is also the same.

That is, except that the colorants are different, the composition for forming the black matrix can have the same formulation as the first composition, and a preferable aspect thereof is also the same.

The method of preparing the composition for forming a black matrix is the same as the method of preparing the first composition, and a preferable aspect thereof is also the same.

[Coloration Film Forming Step]

In the method of manufacturing a color filter, first, it is preferable to form a coloration film (composition layer) including a composition by applying the above composition (one or more kinds of first to fourth compositions) by a predetermined method on the support directly or via another layer. If necessary, the formed coloration film may be dried by performing preliminary curing (prebaking).

Examples of the method of applying the composition on the support include a coating method such as spin coating, slit coating, cast coating, roll coating, bar coating, and inkjet. Among methods by slit coating, a method (hereinafter, referred to as a slit nozzle coating method) of using a slit nozzle such as a slit and spin method or a spinless coating method is preferable. In the slit nozzle coating method, although the conditions of the slit and spin coating method and the spinless coating method vary depending on a size of a coating substrate, for example, in a case where the fifth generation glass substrate (1,100 mm×1,250 mm) is coated with the composition by the spinless coating method, a jetting amount of the composition from a slit nozzle is preferably 500 µl/sec to 2,000 µl/sec and more preferably 800 µl/sec to 1,500 µl/sec. The coating speed is usually 50 mm/sec to 300 mm/sec and preferably 100 mm/sec to 200 mm/sec.

The above application may be performed, for example, for each compartment of the support separated by a black matrix. That is, a composition applied to a certain separated compartment and a composition applied to another compartment may be compositions different from each other.

The concentration of solid content of the composition is preferably 10 mass % to 20 mass % and more preferably 13 mass % to 18 mass %.

After the coloration film is formed, it is preferable to perform a prebaking treatment, and if necessary, a vacuum treatment may be performed before the prebaking treatment. With respect to a condition of vacuum drying, a vacuum degree is preferably 13.33 Pa (0.1 torr) to 133.32 Pa (1.0 torr) and more preferably 26.66 Pa (0.2 torr) to 66.66 Pa (0.5 torr). The prebaking treatment can be performed by using a hot plate, an oven, or the like, at a temperature range of 50° C. to 140° C. and preferably of about 70° C. to 110° C., for 10 seconds to 300 seconds. In the prebaking treatment, a high frequency treatment may be used in combination with the heat treatment. Moreover, in a case where the composition layer applied on the support is dried, it is also possible to perform high frequency treatment alone instead of a prebaking treatment.

The thickness of the coloration film formed with the composition is appropriately selected according to the purpose. In a color filter for a liquid crystal display device, the thickness is preferably in the range of 0.2 µm to 5.0 µm, more preferably in the range of 1.0 µm to 4.0 µm, and most preferably in the range of 1.5 µm to 3.5 µm. In a color filter for a solid-state imaging device, the thickness is preferably in the range of 0.2 µm to 5.0 µm, more preferably in the range of 0.3 µm to 2.5 µm, and most preferably in the range of 0.3 µm to 1.5 µm. The thickness of the coloration film is a film thickness after prebaking.

[Coloration Pattern Forming Step]

In the coloration pattern forming step, pattern shape exposure (pattern exposure) and development are performed on a coloration film (composition layer) formed on a support (for example, a substrate).

The pattern exposure is performed by light irradiation via a photo mask. The exposure can be performed while causing nitrogen gas to flow into a chamber in order to suppress the oxidative discoloration of the colorant in the coloration film.

Light or radiation applicable to exposure is preferably g rays, h rays, i rays, j rays, KrF light, and ArF light, and particularly preferably i rays. In a case where i rays are used as the irradiation light, it is preferable to perform irradiation in an exposure amount of 100 mJ/cm$^2$ to 10,000 mJ/cm$^2$. As the light source, ultra-high pressure, high-pressure, medium-pressure and low-pressure mercury lamps, a chemical lamp, a carbon arc lamp, a xenon lamp, a metal halide lamp, various visible and ultraviolet laser light sources, a fluorescent lamp, a tungsten lamp, sunlight, and the like may be used.

In the exposure method using a laser light source, it is preferable to use an ultraviolet light laser as the light source. The irradiation light is preferably an ultraviolet light laser in a wavelength range in the range of 300 nm to 380 nm and more preferably an ultraviolet light laser at a wavelength in the range of 300 nm to 360 nm, in view of easily matching the photosensitive wavelength of the photopolymerization initiator. Specifically, the third harmonic (355 nm) of an Nd:YAG laser of a relatively inexpensive solid-state laser particularly having a large output and XeCl (308 nm) or XeF (353 nm) of an excimer laser can be appropriately used.

An exposure amount of an object to be exposed (pattern) is in the range of 1 mJ/cm$^2$ to 100 mJ/cm$^2$ and is more preferably in the range of 1 mJ/cm$^2$ to 50 mJ/cm$^2$. It is preferable that exposure amount is this range in view of productivity of pattern formation.

The exposure apparatus is not particularly limited, but commercially available LE5565A (manufactured by Hitachi High-Technologies Corporation), Callisto (manufactured by V Technology Co., Ltd.), EGIS (manufactured by V Technology Co., Ltd.), and DF2200G (manufactured by Dainippon Screen Mfg. Co., Ltd.) can be used. Moreover, apparatuses other than the above can also be used.

In order to apply the method of manufacturing a color filter according to the present embodiment to the manufacturing of a color filter for a liquid crystal display device, an exposure method of performing irradiation mainly with h rays and i rays by a proximity exposure machine and a mirror projection exposure machine is preferable. In a case where the method of manufacturing a color filter according to the present embodiment is applied to the manufacture of a color filter for a solid-state imaging device, an exposure method that performs irradiation mainly with i rays with a stepper exposure device is preferable. In order to manufacture a color filter using a TFT type liquid crystal drive substrate, the photo mask to be used is a photo mask provided with not only a pattern for forming a pixel (coloration pattern) but also a pattern for forming a through hole or a U-shaped depression.

A light emitting diode (LED) and a laser diode (LD) can be used as an actinic radiation source. Particularly, in a case where an ultraviolet light source is required, an ultraviolet LED and an ultraviolet LD can be used. For example, it is possible to a purple LED that is commercially available by Nichia Corporation and that has a main emission spectrum at a wavelength between 365 nm and 420 nm. In a case where an even shorter wavelength is required, examples thereof include an LED disclosed in US6,084,250A that can emit actinic radiation centered between 300 nm and 370 nm. Also, other available UV LEDs may be used. A particularly preferable actinic radiation source is a UV-LED, and among the UV-LEDs, a UV-LED having a peak wavelength between 340 nm and 370 nm is particularly preferable.

Since the ultraviolet light laser has good parallelism, exposure can be performed in a pattern shape without using a mask in a case of exposure. It is preferable that pattern exposure is performed by using a mask, because the linearity of the pattern is further enhanced.

Subsequently, the coloration film after pattern exposure is developed with a developer. Thereby, a coloration pattern can be formed. In development, the coloration film (an uncured portion of the coloration film) in the non-exposed area in pattern exposure is eluted with a developer, such that only the cured portion of the coloration film is left on the substrate.

The development can be performed by a method such as a dip method, a shower method, or a spray method. A swing method, a spin method, an ultrasonic method or the like may be combined. The development may be performed after a treatment of preventing development unevenness by moisturizing a surface to be developed with water or the like in advance before the coloration film comes into contact with a developer. The development treatment may be performed while inclining the support having the coloration film after pattern exposure. In the case of manufacturing a color filter for a solid-state imaging device, so-called paddle development in which a development treatment is performed on a spin coater may be applied.

Any developer can be used as long as the developer dissolves the coloration film in the uncured portion but does not dissolve the cured portion. For example, combinations of various organic solvents and alkaline aqueous solutions can be used. The organic solvents include an organic solvent that can be used in preparing the composition.

Examples of the alkali aqueous solution include alkali aqueous solutions obtained by dissolving alkali compounds such as sodium hydroxide, potassium hydroxide, sodium carbonate, sodium hydrogen carbonate, sodium borate, sodium metaborate, ammonia water, ethylamine, diethylamine, dimethyl ethanolamine, tetramethyl ammonium hydroxide, tetraethylammonium hydroxide, colin, pyrrole, piperidine, and 1,8-diazabicyclo-[5,4,0]-7-undecene such that the concentration becomes 0.001 mass % to 10 mass % and preferably 0.01 mass % to 1 mass %. In this case, the alkali concentration is adjusted to be preferably pH 11 to pH 13 and more preferably pH 11.5 to pH 12.5.

An appropriate amount of, for example, a water-soluble organic solvent such as methanol or ethanol or a surfactant may be added to the alkali aqueous solution.

The development temperature is preferably in the temperature range of 20° C. to 30° C., and the development time is preferably in the range of 20 seconds to 90 seconds.

After the development treatment, it is preferable to perform a rinse treatment to remove the excess developer by washing. The rinse treatment is generally performed with pure water, but in order to save liquid, used pure water may be used at the initial stage of washing, and a treatment is performed with unused pure water for completion. Washing may be performed while the substrate is inclined, or ultrasonic irradiation may be used in combination.

After the rinsing treatment, drying is performed, and then a heat treatment (post-baking) is preferably performed, in order to accelerate curing. Post-baking is preferably performed by a heat treatment at about 150° C. to 250° C. Post-baking can be performed continuously or batchwise by using heating means such as a hot plate, a convection oven (hot air circulation type dryer), and a high frequency heater such that the coated film after development is in the above conditions.

A color filter in which coloration patterns in a plurality of colors are formed as coloration pixels can be manufactured by repeating the above steps sequentially for each color according to the desired number of hues.

In addition to the above steps, in the method of manufacturing a color filter according to the present embodiment, the formed coloration pattern may be further irradiated with ultraviolet light for performing post-exposure.

A heat treatment may be further performed on the coloration pattern subjected to the post-exposure. The colored pattern can be further cured by performing the heating treatment. The heat treatment is performed by, for example, a hot plate, various heaters, or an oven. The temperature during the heat treatment is preferably 100° C. to 300° C. and more preferably 150° C. to 250° C. The heating time is preferably 10 minutes to 120 minutes.

In a case where the composition is applied to the substrate to form a coloration film, the dry thickness of the coloration film is preferably 0.3 µm to 5.0 µm, more preferably 0.5 µm to 3.5 µm, and even more preferably 1.0 µm to 2.5 µm.

(Hemoglobin Sensor)

The color filter according to the present embodiment can be preferably used as a hemoglobin sensor application. Examples of the hemoglobin sensor include a solid-state imaging device which has the color filter relating to the present embodiment.

The configuration of the solid-state imaging device is a configuration provided with the color filter according to the present embodiment, and the configuration is not particularly limited as long as the configuration functions as a solid-state imaging device, but examples thereof include the following configuration.

The configuration has a transfer electrode including a plurality of photodiodes and polysilicon for constituting a light receiving area of a solid-state imaging device (such as a charge-coupled device (CCD) image sensor and a complementary metal oxide semiconductor (CMOS) image sensor) on the support, has a photodiode and a light shielding film formed of tungsten, in which only a light receiving section of the photodiode is opened on the transfer electrode, has a device protective film formed of silicon nitride, which is formed so as to shield the entire surface of the light shielding film and the photodiode light receiving section on the light shielding film, and has the color filter according to the present embodiment on the device protective film.

The photodiode is preferably a photodiode sensitive to a wavelength (400 nm to 700 nm) in the visible region, and examples thereof include a silicon photodiode (SiPD).

The configuration may have a light collecting means (such as a microlens) on the device protective layer and under the color filter (closer to the support, the same is applied below) or may have light collecting means on the color filter.

EXAMPLES

Hereinafter, the embodiment of the present invention is specifically described with reference to the examples. The materials, the amount of use, the proportion, the treatment content, the treatment procedure, and the like provided in the following examples can be appropriately changed without departing from the gist of the present disclosure. The scope of the present disclosure should not be limited by the following specific examples. Unless described otherwise, "parts" and "%" are based on mass.

(Preparation of Pigment Dispersion Composition)
<Preparation of Green Pigment Dispersion Composition (G-1)>

A green pigment dispersion composition (G-1) was prepared in the following order. First, a mixture of the following formulation was uniformly stirred and mixed, and then mixed and dispersed for three hours with a bead mill so as to prepare the green pigment dispersion composition (G-1).

[Formulation]
C. I. Pigment Green 58 (PG58): 9.2 parts by mass
C. I. Pigment Yellow 185 (PY185): 3.5 parts by mass
The following resin B (30 mass % propylene glycol monomethyl ether acetate (PGMEA) solution): 4.9 parts by mass (nonvolatile content)
PGMEA: 82.4 parts by mass hours with a bead mill so as to prepare the orange pigment dispersion composition (Or-1).

[Formulation]
C. I. Pigment Orange 71 (POr71): 12.2 parts by mass
Resin B (30 mass % PGMEA solution): 5.0 parts by mass (nonvolatile content)
PGMEA: 82.8 parts by mass
<Preparation of Orange Pigment Dispersion Composition (Or-2)>

A mixture of the following formulation was uniformly stirred and mixed, and then mixed and dispersed for three hours with a bead mill so as to prepare the orange pigment dispersion composition (Or-2).

[Formulation]
C. I. Pigment Orange 38 (POr38): 12.2 parts by mass
Resin B (30 mass % PGMEA solution): 5.0 parts by mass (nonvolatile content)
PGMEA: 82.8 parts by mass
<Preparation of Yellow Pigment Dispersion Composition (Y-1)>

A mixture of the following formulation was uniformly stirred and mixed, and then mixed and dispersed for three hours with a bead mill so as to prepare the yellow pigment dispersion composition (Y-1).

[Formulation]
C. I. Pigment Yellow 139 (PY139): 12.44 parts by mass
Resin B (30 mass % PGMEA solution): 3.87 parts by mass (nonvolatile content)

Resin B

In the above chemical formulae, the subscripts in parentheses representing constituent units represent content ratios (molar ratios) of the constituent units, and the subscripts in parentheses representing polyester units represent the numbers of repetitions.

The resin B corresponds to the above alkali soluble resin.
<Preparation of Green Pigment Dispersion Composition (G-2)>

A mixture of the following formulation was uniformly stirred and mixed, and then mixed and dispersed for three hours with a bead mill so as to prepare the green pigment dispersion composition (G-2).

[Formulation]
C. I. Pigment Green 36 (PG36): 11.5 parts by mass
Resin B (30 mass % PGMEA solution): 8.0 parts by mass (nonvolatile content)
PGMEA: 80.5 parts by mass
<Preparation of Orange Pigment Dispersion Composition (Or-1)>

A mixture of the following formulation was uniformly stirred and mixed, and then mixed and dispersed for three PGMEA: 83.69 parts by mass
<Preparation of Blue Pigment Dispersion Composition (B-1)>

A mixture of the following formulation was uniformly stirred and mixed, and then mixed and dispersed for three hours with a bead mill so as to prepare the blue pigment dispersion composition (B-1).

[Formulation]
C. I. Pigment Blue 15:6 (PB15:6): 10.2 parts by mass
C. I. Pigment Violet 23 (PV23): 2.6 parts by mass
Disperbyk 111 (manufactured by BYK Japan KK): 2.0 parts by mass (nonvolatile content)
PGMEA: 85.2 parts by mass
<Preparation of Red Pigment Dispersion Composition (R-1)>

A mixture of the following formulation was uniformly stirred and mixed, and then mixed and dispersed for three hours with a bead mill so as to prepare the red pigment dispersion composition (R-1).

[Formulation]

C. I. Pigment Red 177 (PR177): 12.6 parts by mass

Resin B (30 mass % PGMEA solution): 4.6 parts by mass (nonvolatile content)

PGMEA: 82.1 parts by mass

<Preparation of Red Pigment Dispersion Composition (R-2)>

A mixture of the following formulation was uniformly stirred and mixed, and then mixed and dispersed for three hours with a bead mill so as to prepare the red pigment dispersion composition (R-2).

[Formulation]

C. I. Pigment Red 254 (PR254): 12.6 parts by mass

Resin B (30 mass % PGMEA solution): 4.6 parts by mass (nonvolatile content)

PGMEA: 82.1 parts by mass

<Preparation of Red Pigment Dispersion Composition (R-3)>

A mixture of the following formulation was uniformly stirred and mixed, and then mixed and dispersed for three hours with a bead mill so as to prepare the red pigment dispersion composition (R-3).

[Formulation]

C. I. Pigment Red 264 (PR264): 12.6 parts by mass

Resin B (30 mass % PGMEA solution): 4.6 parts by mass (nonvolatile content)

PGMEA: 82.1 parts by mass (Preparation of Composition)

<Preparation of Composition (580-A)>

A composition (580-A) was prepared by uniformly stirring and mixing a mixture of the following formulation.

[Formulation]

Green pigment dispersion composition (G-1): 42.75 parts by mass

Orange pigment dispersion composition (Or-1): 35.77 parts by mass

Resin A: 8.03 parts by mass (40 mass % PGMEA solution)

Photopolymerization initiator (I-1): 1.00 part by mass

Ethylenically unsaturated compound (M-1): 2.08 parts by mass

Fluorine-based surfactant: 4.17 parts by mass (PGMEA solution with nonvolatile content of 0.2 mass %)

PGMEA: 6.20 parts by mass

Details of the compounds in the formulation are as below.

Photopolymerization initiator (I-1): manufactured by BASF SE, IRGACURE OXE02

Ethylenically unsaturated compound (M-1): NK ester A-TMMT (manufactured by Shin-Nakamura Chemical Co., Ltd.)

Fluorine-based surfactant: manufactured by DIC Corporation, MEGAFACE F-781

<Preparation of composition (580-B)>

A composition (580-B) was prepared in the same manner as the composition (580-A), except that the ethylenically unsaturated compound (M-1) was changed to M-350 (manufactured by Toagosei Co., Ltd.).

<Preparation of composition (580-C)>

A composition (580-C) was prepared in the same manner as the composition (580-A), except that the ethylenically unsaturated compound was changed to KAYARAD DPHA (manufactured by Nippon Kayaku Co., Ltd.).

<Preparation of Composition (580-D)>

A composition (580-D) was prepared by uniformly stirring and mixing a mixture of the following formulation.

[Formulation]

Green pigment dispersion composition (G-1): 35.59 parts by mass

Orange pigment dispersion composition (Or-1): 43.90 parts by mass

Resin A: 5.92 parts by mass (40 mass % PGMEA solution)

Photopolymerization initiator (I-1): 1.00 part by mass

Ethylenically unsaturated compound (M-1): 2.08 parts by mass

Fluorine-based surfactant: 4.17 parts by mass (PGMEA solution with nonvolatile content of 1 mass %)

Propylene glycol monomethyl ether acetate (PGMEA): 7.34 parts by mass

<Preparation of Composition (580-E)>

A composition (580-E) was prepared in the same manner as the composition (580-D) except that the orange pigment dispersion liquid was changed to (Or-2).

<Preparation of Composition (500-A)>

A composition (500-A) was prepared by uniformly stirring and mixing a mixture of the following formulation.

[Formulation]

Blue pigment dispersion composition (B-1): 38.55 parts by mass

Yellow pigment dispersion composition (Y-1): 41.78 parts by mass

Resin A: 8.51 parts by mass (40 mass % PGMEA solution)

Photopolymerization initiator (I-1): 1.00 part by mass

Ethylenically unsaturated compound (M-1): 2.08 parts by mass

Fluorine-based surfactant: 4.17 parts by mass (PGMEA solution with nonvolatile content of 0.2 mass %)

PGMEA: 3.91 parts by mass

<Preparation of Composition (540-A)>

A composition (540-A) was prepared by uniformly stirring and mixing a mixture of the following formulation.

[Formulation]

Green pigment dispersion composition (G-2): 42.37 parts by mass

Resin A: 17.63 parts by mass (40 mass % PGMEA solution)

Photopolymerization initiator (I-1): 1.50 parts by mass

Ethylenically unsaturated compound (M-1): 3.11 parts by mass

Fluorine-based surfactant: 4.17 parts by mass (PGMEA solution with nonvolatile content of 0.2 mass %)

PGMEA: 31.22 parts by mass

<Preparation of Composition (600-A)>

A composition (600-A) was prepared by uniformly stirring and mixing a mixture of the following formulation.

Red pigment dispersion composition (R-1): 37.96 parts by mass

Yellow pigment dispersion composition (Y-1): 18.42 parts by mass

Resin A: 8.97 parts by mass (40 mass % PGMEA solution)

Photopolymerization initiator (I-1): 1.13 part by mass

Ethylenically unsaturated compound (M-1): 2.34 parts by mass

Fluorine-based surfactant: 4.17 parts by mass (PGMEA solution with nonvolatile content of 0.2 mass %)

PGMEA: 27.01 parts by mass

<Preparation of Composition (600-B)>

A composition (600-B) was prepared in the same manner as in the composition (600-A) except that the red pigment dispersion composition (R-1) was changed to the red pigment dispersion composition (R-2).

<Preparation of Composition (600-C)>

A composition (600-C) was prepared in the same manner as in the composition (600-A) except that the red pigment dispersion composition (R-1) was changed to the red pigment dispersion composition (R-3).

<Preparation of Composition (600-D)>

A composition (600-D) was prepared by uniformly stirring and mixing a mixture of the following formulation.

Orange pigment dispersion composition (Or-1): 65.04 parts by mass

Yellow pigment dispersion composition (Y-1): 16.13 parts by mass

Resin A: 7.84 parts by mass (40 mass % PGMEA solution, compound having the following structure)

Photopolymerization initiator (I-1): 1.00 part by mass

Ethylenically unsaturated compound (M-1): 2.08 parts by mass

Fluorine-based surfactant: 4.17 parts by mass (PGMEA solution with nonvolatile content of 0.2 mass %)

PGMEA: 3.74 parts by mass

Resin A

[chemical structure]

In the above chemical formulae, subscripts in parentheses representing constitutional units represent a content ratio (molar ratio) of each constitutional unit.

Hereinafter, results evaluated on the absorbance characteristic (absorbance, ratio of absorbance, and minimum absorption wavelength at each wavelength as presented in a table) of each composition are provided.

TABLE 1

| Composition | $A_{500}/B_{580}$ | $C_{600}/B_{580}$ | Minimum absorption wavelength in 400 nm to 700 nm (nm) |
|---|---|---|---|
| 580-A | 4.4 | 1.8 | 580 |
| 580-B | 4.4 | 1.8 | 580 |
| 580-C | 4.4 | 1.8 | 580 |
| 580-D | 4.4 | 1.8 | 580 |
| 580-E | 4.4 | 1.8 | 580 |

TABLE 2

| Composition | $B_{580}/A_{500}$ | $C_{600}/A_{500}$ | Minimum absorption wavelength in 400 nm to 700 nm (nm) |
|---|---|---|---|
| 500-A | 8.5 | 10 | 500 |

TABLE 3

| Composition | $A_{500}/D_{540}$ | $C_{600}/D_{540}$ | Minimum absorption wavelength in 400 nm to 700 nm (nm) |
|---|---|---|---|
| 540-A | 1.9 | 6.1 | 530 |

TABLE 4

| Composition | $A_{500}/C_{600}$ | $B_{580}/C_{600}$ | Minimum absorption wavelength in 400 nm to 700 nm (nm) |
|---|---|---|---|
| 600-A | 9.0 | 5.8 | 700 |
| 600-B | 9.0 | 5.8 | 700 |
| 600-C | 9.0 | 5.8 | 700 |
| 600-D | 9.0 | 5.8 | 700 |

(Evaluation)

Examples 1 to 13

The following evaluation was performed about each composition manufactured as described above.

The evaluation results are provided in Table 1. In examples in which the plurality of color filters are presented, each photosensitive resin composition was patterned by well-known photolithography, and was used in combination.

In each example, a color filter obtained by curing each composition presented in Table 1 was manufactured, and a camera provided with the color filter was manufactured, so as to be used in the following evaluation. As an image sensor of the above camera, an image sensor of a silicon photodiode (SiPD) was used, and a white light source was used as the light source.

A silicon wafer with an undercoat layer was coated with the obtained composition by using a spin coater such that a film thickness after coating was 1.3 μm, and a heat treatment (prebaking) was performed for 120 seconds by using a hot plate at 100° C.

Then, an i rays stepper exposure system FPA-3000i5+ (manufactured by Canon Co., Ltd.) was used, and exposure was performed via a 2.0 μm square island pattern mask or Bayer pattern mask at a wavelength of 365 nm by adjusting an exposure amount such that a pattern size became 2.0 μm square.

Thereafter, the wafer on which the exposed coated film was formed was subjected to paddle development for 60 seconds at 23° C. using a 0.3% aqueous solution of tetramethylammonium hydroxide (TMAH). After that, rinsing was performed with a spin shower, and further washed with pure water, and a heat treatment (post-baking) for 480 seconds using a hot plate at 200° C. was performed, so as to obtain a monochromatic color filter in which a 2.0 μm square island pattern was formed.

With respect to the obtained 2.0 μm square island pattern, a length measurement SEM (S-4800, manufactured by Hitachi, Ltd.) was used, to evaluate the pattern. No residue was observed even in a case where any compositions were used, and a good pattern was formed.

In a case where only one kind of color filter was used, the above lithography process twice using a Bayer pattern mask, so as to form a pattern. More specifically, the second pattern portion was exposed so as to fill the gap between the patterns formed with the Bayer pattern once.

In a case where two kinds of color filters were used, similarly, the second kind of Bayer pattern was formed so as to fill the first kind of Bayer pattern.

In a case where three kinds of color filters were used, one kind (color filter corresponding to the color filter 1) was formed with a Bayer pattern, and then the remaining gaps were filled by performing photolithography twice with an island pattern, so as to form a color filter.

In a case where four kinds of color filters were used, photolithography was performed four times with an island pattern so as to form a color filter.

<<Method of Manufacturing Silicon Wafer with Undercoat Layer>>

The silicon wafer with an undercoat layer used in the evaluation was manufactured as follows.

An 8-inch silicon wafer was uniformly coated with CT-4000L (manufactured by Fujifilm Electromaterials Co., Ltd.) by spin coating so as to form a coated film, and the coated film was cured by performing a treatment for one hour with an oven at 220° C., so as to obtain an undercoat layer. The coating rotation speed of spin coating was adjusted such that the film thickness of the coated film after the above heat treatment was about 0.1 μm.

Comparative Examples 1 to 3

As comparative examples, the following evaluation was performed by using either or both of BPF830 (manufactured by Shibuya Optical Co., Ltd., half-width: 40 nm) which is a band pass filter (BPF) that selectively transmits a wavelength of 830 nm and BPF775 (manufactured by Shibuya Optical Co., Ltd., half-width: 65 nm) which is a BPF that selectively transmits a wavelength of 775 nm.

In the comparative example (Comparative Example 3) in which a BPF was combined, by comparing the contrast of the target regions of the image of the camera provided with each BPF obtained in Comparative Examples 1 and 2, pseudo evaluation was performed on the images that would be obtained by a camera with both of BPF775 and BPF830. An image sensor of SiPD was used as an image sensor of the camera, and a white light source was used as the light source.

The absorbance characteristics of these BPFs were also measured and were presented in Table 5.

TABLE 5

| Color filter | $A_{500}/B_{580}$ | $C_{600}/B_{580}$ | $B_{580}/A_{500}$ | $C_{600}/A_{500}$ |
|---|---|---|---|---|
| BPF830 | 1 | 1 | 1 | 1 |
| BPF775 | 1 | 1 | 1 | 1 |

<Recognition of Hemoglobin>

A camera comprising the color filter according to the embodiment or a camera not comprising a color filter, in which either or both of BPF 830 and BPF 775 which were BPFs of comparative examples were disposed on the light path of the camera was used to photograph a sample obtained by introducing a 2% hemoglobin solution (FUJI-FILM Wako Pure Chemical Corporation) into a 1 cm quartz cell. The hemoglobin solution was photographed in front of a red background paper such that the background was red.

Those with a very clear contrast difference between the hemoglobin solution of the obtained image and the surrounding image area were evaluated as 6, those that could not be identified were evaluated as 1, and those therebetween were evaluated as 5, 4, 3 and 2 points in descending order of evaluation.

The evaluation results were presented in Table 6. In Table 6, the expression "-" indicates that the corresponding filter was not used.

<Identification of Hemoglobin>

The oxygenated hemoglobin solution and the reduced hemoglobin solution were simultaneously photographed by using the camera in which the band pass filter of the comparative example was disposed on an optical path of the camera comprising a color filter of the example or the camera not comprising a color filter, those with a very clear contrast difference were evaluated as 6, those that could not be identified were evaluated as 1, and those therebetween were evaluated as 5, 4, 3 and 2 points in descending order of evaluation.

The evaluation results were presented in Table 6.

TABLE 6

| | Color filter 1 | Color filter 2 | Color filter 3 | Color filter 4 | Other color filter | | Recognition of hemoglobin | Identification of hemoglobin |
|---|---|---|---|---|---|---|---|---|
| Example 1 | 580-A | — | — | — | — | — | 3 | 3 |
| Example 2 | 580-B | — | — | — | — | — | 3 | 3 |
| Example 3 | 580-C | — | — | — | — | — | 3 | 3 |
| Example 4 | 580-D | — | — | — | — | — | 3 | 3 |
| Example 5 | 580-E | — | — | — | — | — | 3 | 3 |
| Example 6 | — | 500-A | — | — | — | — | 2 | 1 |
| Example 7 | 580-A | 500-A | — | — | — | — | 4 | 4 |
| Example 8 | 580-A | — | — | 600-A | — | — | 4 | 5 |
| Example 9 | 580-A | — | 540-A | — | — | — | 4 | 6 |
| Example 10 | — | 500-A | 540-A | — | — | — | 4 | 4 |
| Example 11 | 580-A | 500-A | 540-A | — | — | — | 5 | 6 |
| Example 12 | 580-A | — | 540-A | 600-A | — | — | 5 | 6 |
| Example 13 | 580-A | 500-A | 540-A | 600-A | — | — | 6 | 6 |
| Comparative Example 1 | BPF830 | — | — | — | — | — | 1 | 1 |
| Comparative Example 2 | — | — | — | — | BPF775 | — | 1 | 1 |
| Comparative Example 3 | — | — | — | — | BPF830 | BPF775 | 1 | 1 |

From the above results, it was found that, in a case where the color filter according to the present embodiment using the composition according to the present embodiment was used, hemoglobin by visible light was able to be recognized.

In the case of using the color filter according to the present embodiment, a hemoglobin sensor that is more excellent in hemoglobin recognition than in the case of using a color filter that selectively transmits infrared light was obtained.

Particularly, in the case where at least the color filter 1 was included or at least the color filters 2 and 3 were included, a hemoglobin sensor having excellent identification of hemoglobin was obtained.

It is presumed that this is because the sensitivity of the SiPD to visible light is higher than that of infrared light, and in a white light source, the light amount of visible light is larger than that of infrared light.

The disclosure of JP2017-060057 filed Mar. 24, 2017, is incorporated into the present specification by reference in its entirety.

All documents, patent applications, and technical standards described in the present specification are incorporated into the present specification to the same extent in a case where each individual document, patent application, and technical standard was specifically and individually indicated to be incorporated by reference.

What is claimed is:

1. A composition, comprising:
a green colorant; and
an orange colorant,
wherein, in a case where an absorbance at 500 nm is $A_{500}$, an absorbance at 580 nm is $B_{580}$, and an absorbance at 600 nm is $C_{600}$, $A_{500}/B_{580}$ is 2.0 or more, and $C_{600}/B_{580}$ is 1.5 or more, and
wherein a total content of the green colorant and the orange colorant is 80 mass % or more with respect to a total mass of colorants included in the composition.

2. The composition according to claim 1,
wherein a minimum absorption wavelength is present in a range of 575 nm to 585 nm.

3. The composition according to claim 1, comprising an alkali-soluble resin.

4. The composition according to claim 1, comprising:
a polymerizable compound; and
a photopolymerization initiator.

5. The composition according to claim 1, which is for manufacturing a color filter.

6. A composition, comprising:
a blue colorant; and
a yellow colorant,
wherein an absorbance at 500 nm is $A_{500}$, an absorbance at 580 nm is $B_{580}$, and an absorbance at 600 nm is $C_{600}$, $B580/A_{500}$ is 5.0 or more, and $C_{600}/A_{500}$ is 5.0 or more,
wherein the blue colorant comprises a blue pigment, and
wherein the yellow colorant comprises at least one selected from the group consisting of PY139, PY150, and PY185.

7. The composition according to claim 6,
wherein a minimum absorption wavelength is present in a range of 490 nm to 510 nm.

8. The composition according to claim 6,
wherein a total content of the blue colorant and the yellow colorant is 80 mass % or more with respect to a total mass of colorants included in the composition, and
a mass ratio of the blue colorant and the yellow colorant (the blue colorant:the yellow colorant) is from 70:30 to 30:70.

9. The composition according to claim 6, comprising an alkali-soluble resin.

10. The composition according to claim 6, comprising:
a polymerizable compound; and
a photopolymerization initiator.

11. The composition according to claim 6, which is for manufacturing a color filter.

12. A color filter, comprising a cured product of the composition according to claim 1.

13. The color filter, comprising a cured product of the composition according to claim 6.

14. A color filter, comprising at least two pixels selected from the group consisting of, in a case where an absorbance at 500 nm is $A_{500}$, an absorbance at 580 nm is $B_{580}$, an absorbance at 600 nm is $C_{600}$, and an absorbance at 540 nm is $D_{540}$:
a color filter 1 having $A_{500}/B_{580}$ of 2.0 or more, and $C_{600}/B_{580}$ of 1.5 or more,
a color filter 2 having $B_{580}/A_{500}$ of 5.0 or more, and $C_{600}/A_{500}$ of 5.0 or more,
a color filter 3 having $A_{500}/D_{540}$ of 1.5 or more, and $C_{600}/D_{540}$ of 3.0 or more, and
a color filter 4 having $A_{500}/C_{600}$ of 5.0 or more, and $B_{580}/C_{600}$ of 3.0 or more; and
wherein the color filter at least comprises the color filter 1 or the color filter 2, and
wherein the color filter 2 has a minimum absorption wavelength in a range of 480 nm to 520 nm.

15. The color filter according to claim 14, wherein:
the color filter 1 comprises a green colorant and an orange colorant;
the color filter 2 comprises a blue colorant and an yellow colorant;
the color filter 3 comprises a green colorant; and
the color filter 4 comprises an orange colorant or a red colorant.

16. A hemoglobin sensor, comprising:
the color filter according to claim 14.

17. A hemoglobin sensor, comprising:
the color filter according to claim 15.

* * * * *